(12) United States Patent
Charmley et al.

(10) Patent No.: US 7,622,278 B2
(45) Date of Patent: Nov. 24, 2009

(54) COMPOSITIONS AND METHODS FOR DIAGNOSING OR TREATING PSORIASIS

(75) Inventors: Patrick R. Charmley, Seattle, WA (US); Patrick D. Moss, Shoreline, WA (US); Mark D. McEuen, Seattle, WA (US)

(73) Assignee: UCB SA, Berkshire (GB)

( * ) Notice: Subject to any disclaimer, the term of this patent is extended or adjusted under 35 U.S.C. 154(b) by 0 days.

(21) Appl. No.: 12/218,033

(22) Filed: Jul. 9, 2008

(65) Prior Publication Data
US 2009/0087439 A1 Apr. 2, 2009

Related U.S. Application Data

(63) Continuation of application No. 11/294,760, filed on Dec. 6, 2005, now abandoned, which is a continuation of application No. 09/994,365, filed on Nov. 26, 2001, now Pat. No. 6,989,247.

(60) Provisional application No. 60/253,592, filed on Nov. 28, 2000, provisional application No. 60/256,839, filed on Dec. 15, 2000.

(51) Int. Cl.
*C12N 15/00* (2006.01)

(52) U.S. Cl. .................... 435/69.1; 536/23.1; 435/325; 435/320.1

(58) Field of Classification Search .................... None
See application file for complete search history.

(56) References Cited

OTHER PUBLICATIONS

GenBank Accession No. AC004195, Dec. 8, 1998.*

* cited by examiner

*Primary Examiner*—Misook Yu
(74) *Attorney, Agent, or Firm*—K&L Gates LLP

(57) ABSTRACT

In one aspect, the present invention provides isolated nucleic acid molecules that encode a CAN-1 polypeptide, or an STG polypeptide. In another aspect, the present invention also provides isolated STG polypeptides, isolated CAN-1 polypeptides, and isolated SEEK-1 polypeptides. In another aspect, the present invention provides isolated antibodies that bind specifically to a CAN-1, SEEK-1 or STG polypeptide. In another aspect, the present invention provides methods of diagnosing or predicting the susceptibility to psoriasis of an individual. In another aspect, the present invention provides methods for ameliorating the symptoms and/or progression of psoriasis.

5 Claims, No Drawings

SEQUENCE LISTING

```
<160> NUMBER OF SEQ ID NOS: 16

<210> SEQ ID NO 1
<211> LENGTH: 891
<212> TYPE: DNA
<213> ORGANISM: Homo sapiens
<220> FEATURE:
<221> NAME/KEY: CDS
<222> LOCATION: (64)..(471)

<400> SEQUENCE: 1
```

-continued

```
cctcttgggg ttcccaggca cccagactca gcccacccca gctttggggg ccagtacata    60 gcc atg atc ctc aac tgg aag ctc ctg ggg atc ctg gtc ctt tgc ctg    108
    Met Ile Leu Asn Trp Lys Leu Leu Gly Ile Leu Val Leu Cys Leu
    1               5                   10                  15 cac acc aga ggc atc tca ggc agc gag ggc cac ccc tct cac cca ccc    156
His Thr Arg Gly Ile Ser Gly Ser Glu Gly His Pro Ser His Pro Pro
                20                  25                  30 gca gag gac cga gag gag gca ggc tcc cca aca ttg cct cag ggc ccc    204
Ala Glu Asp Arg Glu Glu Ala Gly Ser Pro Thr Leu Pro Gln Gly Pro
            35                  40                  45 cca gtc ccc ggt gac cct tgg cca ggg gca ccc cct ctc ttt gaa gat    252
Pro Val Pro Gly Asp Pro Trp Pro Gly Ala Pro Pro Leu Phe Glu Asp
        50                  55                  60 cct ccg cct acc cgc ccc agt cgt ccc tgg aga gac ctg cct gaa act    300
Pro Pro Pro Thr Arg Pro Ser Arg Pro Trp Arg Asp Leu Pro Glu Thr
    65                  70                  75 gga gtc tgg ccc cct gaa ccg cct aga acg gat cct cct caa cct ccc    348
Gly Val Trp Pro Pro Glu Pro Pro Arg Thr Asp Pro Pro Gln Pro Pro
80                  85                  90                  95 cgg cct gac gac cct tgg ccg gca gga ccc cag ccc cca gaa aac ccc    396
Arg Pro Asp Asp Pro Trp Pro Ala Gly Pro Gln Pro Pro Glu Asn Pro
                100                 105                 110 tgg cct cct gcc cct gag gtg gac aac cga cct cag gag gag cca gac    444
Trp Pro Pro Ala Pro Glu Val Asp Asn Arg Pro Gln Glu Glu Pro Asp
            115                 120                 125 cta gac cca ccc cgg gaa gag tac aga taatggagtc ccctcagccg          491
Leu Asp Pro Pro Arg Glu Glu Tyr Arg
        130                 135 ttctgttccc aggcatctcc aggcacccac gccctctcca ccctctgatt ccccgtgaat    551
tcttcccaat ttagcctatc tccttaaacc tcttcctcat tccctcggtt ttattctgaa    611
cccgtaaggt ggtgttctca atatttcctg tcccctcctg agatccatac ttagtcctca    671
catcgcccgt ttttcctct gacagcctaa gcctactctc ctacctcgcc tccaggcctc    731
ggccccacct acctcccacc cggtcttcct gcccgcgcga tcgctggggc agggctatgg    791
tactgtgttc ccttctgcca cctggtggcc ggcggcagga actatcagta gacagctgct    851
gcttccatga aacggaaaaa taaaaatcat gttttcttaa                         891
```

<210> SEQ ID NO 2
<211> LENGTH: 136
<212> TYPE: PRT
<213> ORGANISM: Homo sapiens

<400> SEQUENCE: 2

```
Met Ile Leu Asn Trp Lys Leu Leu Gly Ile Leu Val Leu Cys Leu His
1               5                   10                  15

Thr Arg Gly Ile Ser Gly Ser Glu Gly His Pro Ser His Pro Pro Ala
                20                  25                  30

Glu Asp Arg Glu Glu Ala Gly Ser Pro Thr Leu Pro Gln Gly Pro Pro
            35                  40                  45

Val Pro Gly Asp Pro Trp Pro Gly Ala Pro Pro Leu Phe Glu Asp Pro
        50                  55                  60

Pro Pro Thr Arg Pro Ser Arg Pro Trp Arg Asp Leu Pro Glu Thr Gly
65                  70                  75                  80

Val Trp Pro Pro Glu Pro Pro Arg Thr Asp Pro Pro Gln Pro Pro Arg
                85                  90                  95

Pro Asp Asp Pro Trp Pro Ala Gly Pro Gln Pro Pro Glu Asn Pro Trp
```

```
            100                 105                 110
Pro Pro Ala Pro Glu Val Asp Asn Arg Pro Gln Glu Glu Pro Asp Leu
    115                 120                 125

Asp Pro Pro Arg Glu Glu Tyr Arg
    130                 135

<210> SEQ ID NO 3
<211> LENGTH: 114
<212> TYPE: PRT
<213> ORGANISM: Homo sapiens

<400> SEQUENCE: 3

Ser Glu Gly His Pro Ser His Pro Pro Ala Glu Asp Arg Glu Glu Ala
1               5                   10                  15

Gly Ser Pro Thr Leu Pro Gln Gly Pro Val Pro Gly Asp Pro Trp
            20                  25                  30

Pro Gly Ala Pro Pro Leu Phe Glu Asp Pro Pro Thr Arg Pro Ser
        35                  40                  45

Arg Pro Trp Arg Asp Leu Pro Glu Thr Gly Val Trp Pro Pro Glu Pro
    50                  55                  60

Pro Arg Thr Asp Pro Pro Gln Pro Pro Arg Pro Asp Asp Pro Trp Pro
65                  70                  75                  80

Ala Gly Pro Gln Pro Pro Glu Asn Pro Trp Pro Ala Pro Glu Val
            85                  90                  95

Asp Asn Arg Pro Gln Glu Glu Pro Asp Leu Asp Pro Pro Arg Glu Glu
            100                 105                 110

Tyr Arg

<210> SEQ ID NO 4
<211> LENGTH: 3001
<212> TYPE: DNA
<213> ORGANISM: Homo sapiens

<400> SEQUENCE: 4
cctgggatta ccaagaggca tgtgccacca tgtccggcta atattttgt atttttagta      60 gagacggggt ttctccatgt tggtcaggct ggtcttgaac tcccgacctc aggtgatccg    120
cccgcttcgg cctcccaaag tgctgggatt acaggcgcaa gccaccacac caggcccgcg    180
tgatgtatat tttaagacct cttttgctgg tggaggacag gctttgtgtg aggggaggg     240 ataaacagtg ggagcaaggg ggccaattag aagggtgttg gggaggctca ggggagatgg    300
tggctcagga tgatgggctg ggtttggaca gggtgtggag gggcttgcag gtggatggtg    360
gaggagtgta acgaaggttt ctgcgtgagc cctggaggga acagatgaga tcacgccatt    420
gcataataag gtgttcctta ctgtggggta gcggaccagg cagggaacaa cctgggagga    480
atcaaatttt attttggaca tgttacttct gaaaggctaa cagacttcca ggcagaaagg    540
tccttgaggg aaacgttcta ggggtctctc tgggaggctt agatcaagga gctgagacca    600
aaaggagaat gggagggagg agacgagtac aatagagttg gagccaaggt cctagaggcg    660
gataggtgga ttcctgaggg aggaggaagg ggctgaggtt gctggagcct ggcagcttct    720
tccggagcca ttggcaggac tgatgcaaac agctctgggt gggaagaggg aaccaggata    780
tcctcctgtg tccttccttt tctgcagtca tcctgggtgg ctgccagatg gaattccttg    840
gatatcattg cttggaggtc ccctgcatgc ctgaagaagg acatggtgga gagcaggatg    900
cctggatccc atgggggaag ggaagtgccc aggaaagcac gaagcccag ggggagcttt    960
```

| | |
|---|---|
| cagtgcgggg atgagtgggg aggctggggt agtagctgac actgtcccag ctgcatccca | 1020 |
| ggtttgaaag gcacctcctc ccccagcgca ggcatcctgc ctcccaaccc tgtaattacg | 1080 |
| gtgcttccca acgccatcg cgtggtttgc tcccattctt tggcttccaa tagttgcaag | 1140 |
| ggatgaaggt ggacatctct gtgattacgg agatgccaag tgggtattga ctgctccagg | 1200 |
| gtgtggatgg agggtgtgaa aaccagggtg gggtgacgca ggctctgggt catgataggg | 1260 |
| agagcaggca gctgggtcct gggctggagg actaaaataa gggacgccac cttcaggggt | 1320 |
| gacacatcag cccaggcctt cccaacgggt ttgaccagtt ctgttctgat ggtattcctg | 1380 |
| tgccactggg ctggccctc ctccactcct ccctataaa gcctcttggg gttcccaggc | 1440 |
| acccagactc agcccacccc agctttgggg gccagtacat agccatgatc ctcaactgga | 1500 |
| agctcctggg gatcctggtc cttgcctgc acaccagagg tgaggtggga acagaggcag | 1560 |
| ggactgcagt ttggggtgat gagggatact caagatggcg gaggtgaact ggacgcatgg | 1620 |
| ggttggggac aggaattcag gggatgcaga aggtgcatct ggctcaccag aaatggcttt | 1680 |
| ctggacacat tgggtggggg acatggtgca gaaggtgcat ttggctctca ccagaaatgg | 1740 |
| tttgctggct ccatgtggca aagtcggtca ggattaacgt ggggggggac gagtttcctc | 1800 |
| ggagctggga tctgtgttaa ggagctgggt tccttgtaaa gctggggtct gtgtgcctgg | 1860 |
| gggcaaggt gtaacccacc ttgggttgca ggttggcctg aggacaaagc tagtggggta | 1920 |
| ccccaaccag gggtggatgg agcttatttg gagaagtctg gtcagtttaa agtgggtcaa | 1980 |
| gtgaacggtt cagatccatc gggggtaggg gttcatgaca ttttaccatc agttaagtat | 2040 |
| ttacaaacct accgagagct ctttgagagt gacttttttg gtctgtttgt gggtcagttc | 2100 |
| aggctgcgtc catccagaca ggctcctcct cctggggctg gggctgggtg gggctgggga | 2160 |
| gagaagccct caccacctct tacctttctc cttcctcctt tacaggcatc tcaggcagcg | 2220 |
| agggccaccc ctctcaccca cccgcagagg accgagagga ggcaggctcc ccaacattgc | 2280 |
| ctcagggccc cccagtcccc ggtgaccctt ggccagggc acccctctc tttgaagatc | 2340 |
| ctccgcctac ccgccccagt cgtccctgga gagacctgcc tgaaactgga gtctggcccc | 2400 |
| ctgaaccgcc tagaacggat cctcctcaac ctccccggcc tgacgaccct tggccggcag | 2460 |
| gaccccagcc cccagaaaac ccctggcctc ctgcccctga ggtggacaac cgacctcagg | 2520 |
| aggagccaga cctagaccca ccccgggaag agtacagata atggagtccc ctcagccgtt | 2580 |
| ctgttcccag gcatctccag gcacccacgc cctctccacc ctctgattcc ccgtgaattc | 2640 |
| ttcccaattt agcctatctc cttaaacctc ttcctcattc cctcggtttt attctgaacc | 2700 |
| cgtaaggtgg tgttctcaat atttcctgtc ccctcctgag atccatactt agtcctcaca | 2760 |
| tcgcccgttt tttcctctga cagcctaagc ctactctcct acctcgcctc caggcctcgg | 2820 |
| ccccacctac ctcccacccg gtcttcctgc ccgcgcgatc gctggggcag gctatggta | 2880 |
| ctgtgttccc ttctgccacc tggtggccgg cggcaggaac tatcagtaga cagctgctgc | 2940 |
| ttccatgaaa cggaaaaata aaaatcatgt tttcttaatt ctgaatctag gctgctgctt | 3000 |
| t | 3001 |

<210> SEQ ID NO 5
<211> LENGTH: 1145
<212> TYPE: DNA
<213> ORGANISM: Homo sapiens
<220> FEATURE:
<221> NAME/KEY: CDS
<222> LOCATION: (1)..(978)

<400> SEQUENCE: 5

```
atg cag ggc cgc gtg gca ggg agc tgc gct cct ctg ggc ctg ctc ctg      48
Met Gln Gly Arg Val Ala Gly Ser Cys Ala Pro Leu Gly Leu Leu Leu
1               5                   10                  15 gtc tgt ctt cat ctc cca ggc ctc ttt gcc cgg agc atc ggt gtt gtg      96
Val Cys Leu His Leu Pro Gly Leu Phe Ala Arg Ser Ile Gly Val Val
            20                  25                  30 gag gag aaa gtt tcc caa aac ttg ggg acc aac ttg cct cag ctc gga     144
Glu Glu Lys Val Ser Gln Asn Leu Gly Thr Asn Leu Pro Gln Leu Gly
        35                  40                  45 caa cct tcc tcc act ggc ccc tct aac tct gaa cat ccg cag ccc gct     192
Gln Pro Ser Ser Thr Gly Pro Ser Asn Ser Glu His Pro Gln Pro Ala
    50                  55                  60 ctg gac cct agg tct aat gac ttg gca agg gtt cct ctg aag ctc agc     240
Leu Asp Pro Arg Ser Asn Asp Leu Ala Arg Val Pro Leu Lys Leu Ser
65                  70                  75                  80 gtg cct gca tca gat ggc ttc cca cct gca gga ggt tct gca gtg cag     288
Val Pro Ala Ser Asp Gly Phe Pro Pro Ala Gly Gly Ser Ala Val Gln
                85                  90                  95 agg tgg cct cca tcg tgg ggg ctg cct gcc atg gat tcc tgg ccc cct     336
Arg Trp Pro Pro Ser Trp Gly Leu Pro Ala Met Asp Ser Trp Pro Pro
            100                 105                 110 gag gat cct tgg cag atg atg gct gct gcg gct gag gac cgc ctg ggg     384
Glu Asp Pro Trp Gln Met Met Ala Ala Ala Ala Glu Asp Arg Leu Gly
        115                 120                 125 gaa gcg ctg cct gaa gaa ctc tct tac ctc tcc agt gct gcg gcc ctc     432
Glu Ala Leu Pro Glu Glu Leu Ser Tyr Leu Ser Ser Ala Ala Ala Leu
    130                 135                 140 gct ccg ggc agt ggc cct ttg cct ggg gag tct tct ccc gat gcc aca     480
Ala Pro Gly Ser Gly Pro Leu Pro Gly Glu Ser Ser Pro Asp Ala Thr
145                 150                 155                 160 ggc ctc tca ccc gag gct tca ctc ctc cac cag gac tcg gag tcc aga     528
Gly Leu Ser Pro Glu Ala Ser Leu Leu His Gln Asp Ser Glu Ser Arg
                165                 170                 175 cga ctg ccc cgt tct aat tca ctg gga gcc ggg gga aaa atc ctt tcc     576
Arg Leu Pro Arg Ser Asn Ser Leu Gly Ala Gly Gly Lys Ile Leu Ser
            180                 185                 190 caa cgc cct ccc tgg tct ctc atc cac agg gtt ctg cct gat cac ccc     624
Gln Arg Pro Pro Trp Ser Leu Ile His Arg Val Leu Pro Asp His Pro
        195                 200                 205 tgg ggt acc ctg aat ccc agt gtg tcc tgg gga ggt gga ggc cct ggg     672
Trp Gly Thr Leu Asn Pro Ser Val Ser Trp Gly Gly Gly Gly Pro Gly
    210                 215                 220 act ggt tgg gga acg agg ccc atg cca cac cct gag gga atc tgg ggt     720
Thr Gly Trp Gly Thr Arg Pro Met Pro His Pro Glu Gly Ile Trp Gly
225                 230                 235                 240 atc aat aat caa ccc cca ggt acc agc tgg gga aat att aat cgg tat     768
Ile Asn Asn Gln Pro Pro Gly Thr Ser Trp Gly Asn Ile Asn Arg Tyr
                245                 250                 255 cca gga ggc agc tgg gga aat att aat cgg tat cca gga ggc agc tgg     816
Pro Gly Gly Ser Trp Gly Asn Ile Asn Arg Tyr Pro Gly Gly Ser Trp
            260                 265                 270 ggg aat att aat cgg tat cca gga ggc agc tgg ggg aat att cat cta     864
Gly Asn Ile Asn Arg Tyr Pro Gly Gly Ser Trp Gly Asn Ile His Leu
        275                 280                 285 tac cca ggt atc aat aac cca ttt cct cct gga gtt ctc cgc cct cct     912
Tyr Pro Gly Ile Asn Asn Pro Phe Pro Pro Gly Val Leu Arg Pro Pro
    290                 295                 300 ggc tct tct tgg aac atc cca gct ggc ttc cct aat cct cca agc cct     960
Gly Ser Ser Trp Asn Ile Pro Ala Gly Phe Pro Asn Pro Pro Ser Pro
```

```
Gly Ser Ser Trp Asn Ile Pro Ala Gly Phe Pro Asn Pro Pro Ser Pro
305                 310                 315                 320 agg ttg cag tgg ggc tag agcacgatag agggaaaccc aacattggga            1008
Arg Leu Gln Trp Gly
            325 gttagagtcc tgctcccgcc ccttgctgtg tgggctcaat ccaggccctg ttaacatgtt   1068 tccagcacta tccccacttt tcagtgcctc ccctgctcat ctccaataaa ataaaagcac   1128 ttatggaaaa aaaaaaa                                                  1145

<210> SEQ ID NO 6
<211> LENGTH: 325
<212> TYPE: PRT
<213> ORGANISM: Homo sapiens

<400> SEQUENCE: 6

Met Gln Gly Arg Val Ala Gly Ser Cys Ala Pro Leu Gly Leu Leu Leu
1               5                   10                  15

Val Cys Leu His Leu Pro Gly Leu Phe Ala Arg Ser Ile Gly Val Val
            20                  25                  30

Glu Glu Lys Val Ser Gln Asn Leu Gly Thr Asn Leu Pro Gln Leu Gly
        35                  40                  45

Gln Pro Ser Ser Thr Gly Pro Ser Asn Ser Glu His Pro Gln Pro Ala
    50                  55                  60

Leu Asp Pro Arg Ser Asn Asp Leu Ala Arg Val Pro Leu Lys Leu Ser
65                  70                  75                  80

Val Pro Ala Ser Asp Gly Phe Pro Pro Ala Gly Gly Ser Ala Val Gln
                85                  90                  95

Arg Trp Pro Pro Ser Trp Gly Leu Pro Ala Met Asp Ser Trp Pro Pro
            100                 105                 110

Glu Asp Pro Trp Gln Met Met Ala Ala Ala Glu Asp Arg Leu Gly
        115                 120                 125

Glu Ala Leu Pro Glu Glu Leu Ser Tyr Leu Ser Ser Ala Ala Ala Leu
    130                 135                 140

Ala Pro Gly Ser Gly Pro Leu Pro Gly Glu Ser Ser Pro Asp Ala Thr
145                 150                 155                 160

Gly Leu Ser Pro Glu Ala Ser Leu Leu His Gln Asp Ser Glu Ser Arg
                165                 170                 175

Arg Leu Pro Arg Ser Asn Ser Leu Gly Ala Gly Gly Lys Ile Leu Ser
            180                 185                 190

Gln Arg Pro Pro Trp Ser Leu Ile His Arg Val Leu Pro Asp His Pro
        195                 200                 205

Trp Gly Thr Leu Asn Pro Ser Val Ser Trp Gly Gly Gly Pro Gly
    210                 215                 220

Thr Gly Trp Gly Thr Arg Pro Met Pro His Pro Glu Gly Ile Trp Gly
225                 230                 235                 240

Ile Asn Asn Gln Pro Pro Gly Thr Ser Trp Gly Asn Ile Asn Arg Tyr
                245                 250                 255

Pro Gly Gly Ser Trp Gly Asn Ile Asn Arg Tyr Pro Gly Gly Ser Trp
            260                 265                 270

Gly Asn Ile Asn Arg Tyr Pro Gly Gly Ser Trp Gly Asn Ile His Leu
        275                 280                 285

Tyr Pro Gly Ile Asn Asn Pro Phe Pro Pro Gly Val Leu Arg Pro Pro
    290                 295                 300

Gly Ser Ser Trp Asn Ile Pro Ala Gly Phe Pro Asn Pro Pro Ser Pro
```

```
                   305                 310                 315                 320
Arg Leu Gln Trp Gly
            325

<210> SEQ ID NO 7
<211> LENGTH: 5000
<212> TYPE: DNA
<213> ORGANISM: Homo sapiens

<400> SEQUENCE: 7
aacacaggat gcctctagaa ggtgaaaaag cagggaaagg gattttcccc tgaggccccc      60
agaaagaatc acagccctgc tgacaccttt attttaatcc actgagacct gttttagact     120
tctgatctcc aaaactgtaa agtaataaat ccatgttgtt gtaagccatt cggttcatgg     180
taatttgtca ctgcagcagc aggaattagt cagtatctca taaggatggc atccaggtcc     240
atttccctag ctagatccag ggtctcatgt aggagcagct cctcagatgg ggccacttct     300
gcaccccaga acctcctgca ggttggggcc aaggtgaagg agatatgagg atgcatgaga     360 aagggggtgct gggaggaaac aatccagctc caaaaagaa acaagtgttt ctgttgctga     420
gagaggcaat taagagagtg ggaccccagg gtggaggtcc ttgtgtatag agaagcaggg     480
ctggggaggc tggcaaccag ggatgagctg tgagccagga cacctgggcc aagaaggggc     540
agggaggtca aggaaaggag ccagggcggg agacacccag cttcctctgg acattcatt     600 caagtgacac ctgttgccac agaccacatt aggaatgagg gtggaatgtg gagggtttatt    660 gtcttcacaa ccactagccc agcctgtttc tgctgtcccc cacccactac caggataaaa    720
gggctggctg tcttgggct gagggagatc gggtgctgag caggatgcag ggccgcgtgg      780
cagggagctg cgctcctctg ggcctgctcc tggtctgtct tcatctccca ggtatggagg     840
ccgtgatgcc cttgggcagg agggactgga ggtcccccag gaaacaggaa ttaaggaaag     900
gggtaaaggc aggagggtac acatttaggt ccctgaggga aaaggaagaa taggcatagg     960
ggaagcaaag ggaactgggg actcgggac tggagaccac tggttgcttt atcttcccctt     1020 tccctcaggc ctctttgccc ggagcatcgg tgttgtggag gagaaagttt cccaaaactt     1080
ggggaccaac ttgcctcagc tcggacaacc ttcctccact ggcccctcta actctgaaca     1140
tccgcagccc gctctggacc ctaggtctaa tgcttggca agggttcctc tgaagctcag      1200
cgtgcctgca tcagatggct tcccacctgc aggaggttct gcagtgcaga ggtggcctcc     1260
atcgtggggg ctgcctgcca tggattcctg gccccctgag gatccttggc agatgatggc     1320
tgctgcggct gaggaccgcc tgggggaagc gctgcctgaa gaactctctt acctctccag     1380
tgctgcggcc ctcgctccgg gcagtggccc tttgcctggg gagtcttctc ccgatgccac    1440
aggcctctca cccaaggctt cactcctcca ccaggactcg gagtccagac gactgccccg    1500
ttctaattca ctgggagccg gggaaaaat cctttcccaa cgccctccct ggtctctcat     1560
ccacagggtt ctgcctgatc acccctgggg taccctgaat cccagtgtgt cctggggagg    1620 tggaggcccct gggactggtt ggggaacgag gcccatgcca cacctgagg gaatctgggg    1680 tatcaataat caacccccag gtaccagctg ggaaatatt aatcggtatc caggaggcag     1740
ctggggaaat attaatcggt atccaggagg cagctggggg aatattaatc ggtatccagg    1800
aggcagctgg gggaatattc atctatacc aggtatcaat aacccattc ctcctggagt      1860 cctccgccct cctggctctt cttgaacat cccagctggc ttccctaatc ctccaagccc     1920
taggttgcag tggggctaga gcacgataga gggaaaccca acattgggag ttagagtcct    1980
```

```
gctcccgccc cttgctgtgt gggctcaatc caggccctgt cagcatgttt ccagcactat   2040
ccccactttt cagtgcctcc cctgctcatc tccaataaaa taaaagcact tatggaattt   2100
gcttctcctt ggtttctttg tttctgggca taagctgaag tgagtctggg cataagctga   2160
agtgagtctg ttcattcctg ttttctagcc atccccacgg ccctctaggg gcccctgcag   2220
acgctgtctt gctatcccca tccttcacaa aggatcagtg cccaagtgct tgagggtgga   2280
gcctcagtct caccccggcc aggtgggaga gctgttccag aattgtgctg gaatctgaaa   2340
gggggaggag ggacagcagg actaattgag atggcacctg cagcaggggg caaggatgag   2400
gtcccagaag gcggctccag ggccaggtgg acaggattcc ttgcaactca cagaaacagg   2460
aagccaaaag tcgcaatgtc tacgcttcac ttgtcttttc ttccccggaa agtcaagctt   2520 cttgaagtg gaggtacatc gacctcctcc cttacaggca tcatttagca cattgtgtcc   2580
cacagaacca cagactttga agagttgctg agtaaatagc agacctcgat aaaggaaaag   2640
agaaagggaa gaaaggaaag ggagaaaaaa accttgaagc caacaatccc acctggggtg   2700
gcatttgatg ctttcattcc caagtgatga cacagtctca gcctttggtc acagtattgt   2760
ctctcctgcc ctcccttcgg ttttcccagg agctcaacat cctcacacag gagttggagt   2820
gacggcagcg aagggtcagg ctacaaaagc acggaagaat cagcaggtgt gggttggagg   2880
tgatttgggt ctggattctc tcttccctgt gccatgcctg cagtggtcca ggtgtatgta   2940
ctctccatcc agtcaggtcc ctgggagttg ggcagcttgt gggaggggag aaaggagtag   3000
gaaaaacacc agaactcaag gggtagggag ctgcctgcct gcctgcctga gtggcagatg   3060
ggcatttctg gagaagatgc ccggtcccag cgtctgccat aaggctccat cctacactga   3120
gaagtccttc ctggaacacc ttcctcagag cccacctttc ccatcaccaa gcacactccc   3180
ttcgtcaaca cctcaacctc ctcacctgat tcttttccca gcttggactc tcttggtttc   3240
tccctgccct agggcaaggg gttccatgcc tgttttcagc acctgcctct tccaccagcc   3300
caaggtcatt ctatcaagcc tggagtctca tttctctctg tccctcttcc tggtggcctc   3360
ttctgcatag tcattcctat tcgcacattt aaatttggtg tcaacagtcc cctgctctgt   3420
tccacagact cactagagca taagcaccac gaggacaggg gctttgtctc tttagttcac   3480
tgctgcaccc ccagcacaaa gaacagggtc tggaccaggg caggcactca gcaggcacga   3540
aggaatggct gatcctctct ctctgtccct cccctctct catcatctct cttcttccac   3600
tcaattcctg agccatgcgg ctacacccag agtctaatct acactccggc tgtagccctc   3660
ccagagcctc actgacattt ttcaacaacc tcatgaagcc cttctcagca ttaaaatgct   3720
ctgtgcgttt catcatttaa ccttcattat tctctgtgag gaaggcatta taagattttt   3780
gcggccaggc acgtggctc acacctgtaa tcccagcact ttgggagaac gaggcaggcg   3840
gatcacctga ggagttcgag acagcctagt ccaacatggg gaacatggtg aaacctcatc   3900
tctactaaaa acacaaaaat tagccaggca tggtgcctgt aatgccagct acttaggagg   3960
ctgaggctgg agaatcgctt gaacccggga gttggaggtt gtagtgagcc gagatcgcgc   4020
cactgcactc cagcctgggt gacagagcga gactccgtct caaaaaaaaa aaagattttt   4080
tacagatgga ggaactgaga tttagaggga ttaagcaagt cacacagggt tacaagtgac   4140
aggggtggtg actcaaacct catttttctc attatctgtc cagggagtat tcaagtacaa   4200
tatgcaatta acagaaataa caacgaactt ttattatatt tacatatagg ccaggtcctg   4260
gacaaggggc ttgcacacac cccttccag caaatcctca caacacccc attgggtggg   4320 cactgcgggg catactgcac agggaagaca ctgaggccca gagaggatgg ggagctgagg   4380
```

-continued

```
ctcacacaca ggcaacactg agccagggca gtgaagttca tctgatgctt ggtgctgatg      4440 gctcaggga a gatggacttt aacagtggag ggtcccaggg ggatgtggcc agtcccctca     4500
gggtggtctt tggattaacg ttagttgttg cttaaaaaat ggtggaactg ggcatggtgg      4560
ctcatgtctg taatttcagc actttgggag ctgaggcagg aggattactt gagcccagga      4620
attctagacc agcctgggca acataggagc cctcatctc tacaaatagt aattaaaaaa      4680
ttagcttgag cacttaaaaa aaaaattaag agtaggccgg gcatggtggc tcacacctgt      4740
aatcccaaca ctttgggagg ccaaggcagg tggagaccag cctggccaat gtggtgaaac      4800
cccatctcta ctaaaaatac aaaaattagc caggcatggt gttgcacgcc tgtaatccca      4860
gctagaggga aggctgaggt ataagaattg cttgaacttg ggagatggag gttgcagtga      4920
gctgagattg tgccactgca ctccagcctg ggcaacagag tgagactctg tctcaaaaaa      4980
aaaatcatca tcataagagc                                                  5000
```

<210> SEQ ID NO 8
<211> LENGTH: 861
<212> TYPE: DNA
<213> ORGANISM: Homo sapiens
<220> FEATURE:
<221> NAME/KEY: CDS
<222> LOCATION: (275)..(733)

<400> SEQUENCE: 8

```
caggaaatcg agactcatga ctcccagaga ggatggcatc tagaagtaga cgatcaaggg       60
tggaatctac agtccatggg ccctgacttc ttgccttcgt ctcaaataga ctctgcagcc      120
agccatctat gcagcgcccc agtggctttg aaatgcaaca gaaaccatca cccccggacc      180
gtgggctcca tgccagtggg caaagcacag cctgggaaga attggtttgc agccaggcag      240
tcctccatcc agtcttgact ttggcacttg tgat atg act tgc aca gac caa aaa      295
                                    Met Thr Cys Thr Asp Gln Lys
                                    1               5 agt cac tct caa aga gct ctc ggc aca cag acc cca gct tta caa gga       343
Ser His Ser Gln Arg Ala Leu Gly Thr Gln Thr Pro Ala Leu Gln Gly
        10                  15                  20 ccc cag ctc ctt aac aca gat ccc agc tcc aag gaa act cgt ccc ccc       391
Pro Gln Leu Leu Asn Thr Asp Pro Ser Ser Lys Glu Thr Arg Pro Pro
    25                  30                  35 cac gtt aat cct gac cga ctt tgc cac atg gag cca gca aac cat ttc       439
His Val Asn Pro Asp Arg Leu Cys His Met Glu Pro Ala Asn His Phe
40                  45                  50                  55 tgg cat gca ggg gac ctc caa gca atg ata tcc aag gaa ttc cat ctg       487
Trp His Ala Gly Asp Leu Gln Ala Met Ile Ser Lys Glu Phe His Leu
                60                  65                  70 gca gcc acc cag gat gac tgc aga aaa gga agg aca cag gag gat atc       535
Ala Ala Thr Gln Asp Asp Cys Arg Lys Gly Arg Thr Gln Glu Asp Ile
            75                  80                  85 ctg gtt ccc tct tcc cac cca gag ctg ttt gca tca gtc ctg cca atg       583
Leu Val Pro Ser Ser His Pro Glu Leu Phe Ala Ser Val Leu Pro Met
        90                  95                  100 gct ccg gaa gaa gct gcc agg ctc cag caa cct cag ccc ctt cct cct       631
Ala Pro Glu Glu Ala Ala Arg Leu Gln Gln Pro Gln Pro Leu Pro Pro
    105                 110                 115 ccc tca gga atc cac cta tcc gcc tct agg acc ttg gct cca act cta       679
Pro Ser Gly Ile His Leu Ser Ala Ser Arg Thr Leu Ala Pro Thr Leu
120                 125                 130                 135
```

```
ttg tac tcg tct cct ccc tcc cat tct cct ttt ggt ctc agc tcc ttg      727
Leu Tyr Ser Ser Pro Pro Ser His Ser Pro Phe Gly Leu Ser Ser Leu
            140                 145                 150 atc taa gcctcccaga gagacccta gaatgtttcc ctcaaggacc tttctgcctg        783
Ile gaagtctgtt agcctttcag aagtaacatg tccaaaataa aatttgattc ctcccaggtt    843
gttccctgcc tggtccgc                                                  861

<210> SEQ ID NO 9
<211> LENGTH: 152
<212> TYPE: PRT
<213> ORGANISM: Homo sapiens

<400> SEQUENCE: 9

Met Thr Cys Thr Asp Gln Lys Ser His Ser Gln Arg Ala Leu Gly Thr
1               5                   10                  15

Gln Thr Pro Ala Leu Gln Gly Pro Gln Leu Leu Asn Thr Asp Pro Ser
            20                  25                  30

Ser Lys Glu Thr Arg Pro Pro His Val Asn Pro Asp Arg Leu Cys His
        35                  40                  45

Met Glu Pro Ala Asn His Phe Trp His Ala Gly Asp Leu Gln Ala Met
    50                  55                  60

Ile Ser Lys Glu Phe His Leu Ala Ala Thr Gln Asp Asp Cys Arg Lys
65                  70                  75                  80

Gly Arg Thr Gln Glu Asp Ile Leu Val Pro Ser Ser His Pro Glu Leu
                85                  90                  95

Phe Ala Ser Val Leu Pro Met Ala Pro Glu Glu Ala Ala Arg Leu Gln
            100                 105                 110

Gln Pro Gln Pro Leu Pro Pro Ser Gly Ile His Leu Ser Ala Ser
        115                 120                 125

Arg Thr Leu Ala Pro Thr Leu Leu Tyr Ser Ser Pro Pro Ser His Ser
    130                 135                 140

Pro Phe Gly Leu Ser Ser Leu Ile
145                 150

<210> SEQ ID NO 10
<211> LENGTH: 2997
<212> TYPE: DNA
<213> ORGANISM: Homo sapiens

<400> SEQUENCE: 10
cctgggatta caggcatgtg ccaccatgtc cggctaatat ttttgtattt ttagtagaga     60
cggggtttct ccatgttggt caggctggtc ttgaactccc gacctcaggt gatccgcccg    120
cttcggcctc ccaaagtgct gggattacag gcgcaagcca ccacaccagg cccgcgtgat    180
gtatatttta agacctcttt tgctggtgga ggacaggctt tgtgtgaggg ggagggataa    240
acagtgggag caaggggggcc aattagaagg gtgttgggga ggctcagggg agatggtggc    300
tcaggatgat gggctgggtt tggacagggt gtgagggggc ttgcaggtgg atggtggagg    360
agtgtaacga aggtttctgc gtgagccctg gaggaacag atgagatcac gccattgcat    420
aataaggtgt tccttactgt ggggtagcgg accaggcagg gaacaacctg ggaggaatca    480
aattttattt tggacatgtt acttctgaaa ggctaacaga cttccaggca gaaaggtcct    540
tgagggaaac gttctagggg tctctctggg aggcttagat caaggagctg agaccaaaag    600
gagaatggga gggaggagac gagtacaata gagttggagc caaggtccta gaggcggata    660
ggtggattcc tgaggagga ggaagggggct gaggttgctg gagcctggca gcttcttccg    720
```

```
gagccattgg caggactgat gcaaacagct ctgggtggga agagggaacc aggatatcct    780
cctgtgtcct tccttttctg cagtcatcct gggtggctgc cagatggaat tccttggata    840
tcattgcttg gaggtcccct gcatgcctga agaaggacat ggtggagagc aggatgcctg    900
gatcccatgg gggaagggaa gtgcccagga agcacgaag ccccaggggg agctttcagt     960
gcggggatga gtgggaggc tggggtagta gctgacactg tcccagctgc atcccaggtt    1020
tgaaaggcac ctcctccccc agcgcaggca tcctgcctcc caaccctgta attacggtgc    1080
ttcccaacgc ccatcgcgtg gtttgctccc attctttggc ttccaatagt tgcaagggat    1140
gaaggtggac atctctgtga ttacggagat gccaagtggg tattgactgc tccagggtgt    1200
ggatggaggg tgtgaaaacc agggtgtggg gacgcaggct ctgggtcatg atagggagag    1260
caggcagctg ggtcctgggc tggaggacta aaataaggga cgccaccttc aggggtgaca    1320
catcagccca ggccttccca acgggtttga ccagttctgt tctgatggta ttcctgtgcc    1380
actgggctgg cccctcctcc actcctcccc tataaagcct cttggggttc ccaggcaccc    1440
agactcagcc caccccagct ttgggggcca gtacatagcc atgatcctca actgaagct     1500 cctggggatc ctggtccttt gcctgcacac cagaggtgag gtgggaacag aggcagggac    1560
tgcagtttgg ggtgatgagg gatactcaag atggcggagg tgaactggac gcatgggttt    1620
ggggacagga attcagggga tgcagaaggt gcatctggct caccagaaat ggctttctgg    1680
acacattggg tggggacat ggtgcagaag gtgcatttgg ctctcaccag aaatggtttg     1740
ctggctccat gtggcaaagt cggtcaggat taacgtgggg gggacgagt ttcctcggag     1800 ctgggatctg tgttaaggag ctgggttcct tgtaaagctg gggtctgtgt gcctggggc     1860 caaggtgtaa cccaccttgg gttgcaggtt ggcctgagga caaagctagt ggggtacccc    1920
aaccaggggt ggatggagct tatttggaga agtctggtca gtttaaagtg ggtcaagtga    1980
acggttcaga tccatcgggg gtaggggttc atgacatttt accatcagtt aagtatttac     2040
aaacctaccg agagctcttt gagagtgact ttttggtct gtttgtgggt cagttcaggc      2100
tgcgtccatc cagacaggct cctcctcctg gggctggggc tggtggggc tgggagaga      2160 agccctcacc acctcttacc tttctccttc ctcctttaca ggcatctcag gcagcgaggg    2220 ccaccccttct cacccacccg cagaggaccg agaggaggca ggctcccaa cattgcctca    2280 gggcccccca gtccccggtg acccttggcc aggggcaccc cctctctttg aagatcctcc    2340 gcctaccgc cccagtcgtc cctggagaga cctgcctgaa actggagtct ggcccccctga    2400 accgcctaga acggatcctc ctcaacctcc ccggcctgac gacccttggc cggcaggacc    2460
ccagccccca gaaaccccct ggcctcctgc ccctgaggtg acaaccgac ctcaggagga     2520 gccagaccta gacccacccc gggaagagta cagataatgg agtcccctca gccgttctgt    2580
tcccaggcat ctccaggcac ccacgccctc tccaccctct gattcccgt gaattcttcc     2640 caatttagcc tatctcctta aacctcttcc tcattccctc ggttttattc tgaacccgta    2700
aggtggtgtt ctcaatattt cctgtcccct cctgagatcc atactagtc ctcacatcgc     2760 ccgttttttc ctctgacagc ctaagcctac tctcctacct cgcctccagg cctcggcccc    2820
acctacctcc cacccggtct tcctgcccgc gcgatcgctg gggcagggct atggtactgt    2880
gttcccttct gccacctggt ggccggcggc aggaactatc agtagacagc tgctgcttcc    2940
atgaaacgga aaaataaaaa tcatgttttc ttaattctga atctaggctg ctgcttt      2997
```

<210> SEQ ID NO 11

```
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: PCR Primer DMO 9299

<400> SEQUENCE: 11
gactcagccc accccagctt t                                              21

<210> SEQ ID NO 12
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: PCR Primer DMO 8932

<400> SEQUENCE: 12
ccggggtggg tctaggtct                                                 19

<210> SEQ ID NO 13
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: PCR Primer DMO 14104

<400> SEQUENCE: 13
tcctctgggc ctgctcct                                                  18

<210> SEQ ID NO 14
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: PCR Primer DMO 14030

<400> SEQUENCE: 14
gtccgagctg aggcaagttg                                                20

<210> SEQ ID NO 15
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: PCR Primer DMO 14027

<400> SEQUENCE: 15
ggaaccagga tatcctcctg tgt                                            23

<210> SEQ ID NO 16
<211> LENGTH: 23
<212> TYPE: DNA
<213> ORGANISM: Artificial Sequence
<220> FEATURE:
<221> NAME/KEY: misc_feature
```

-continued

```
<222> LOCATION: (1)..(23)
<223> OTHER INFORMATION: PCR Primer DMO 14102

<400> SEQUENCE: 16
accccagctc cttaacacag atc                                              23
```

COMPOSITIONS AND METHODS FOR DIAGNOSING OR TREATING PSORIASIS

RELATED APPLICATIONS

The present invention claims benefit of priority from U.S. patent application Ser. No. 11/294,760 filed Dec. 6, 2005, which claims benefit of priority from U.S. patent application Ser. No. 09/994,365 filed Nov. 6, 2001, which claims benefit from U.S. Provisional Application No. 60/253,592 filed Nov. 28, 2000, and U.S. Provisional No. 60/256,839 filed Dec. 15, 2000, under 35 U.S.C. § 119. The foregoing provisional patent applications are incorporated herein by reference in their entirety.

FIELD OF THE INVENTION

The present invention relates generally to polynucleotides, polypeptides, antibodies and methods for the diagnosis of psoriasis, and/or the amelioration of the symptoms of psoriasis.

BACKGROUND OF THE INVENTION

Psoriasis is a chronic inflammatory dermatosis that affects about 2% of the Caucasian population. It is characterized by hyperproliferation of epidermal cells and inflammation resulting from infiltration of activated T-helper cells and mononuclear cells and release of pro-inflammatory cytokines (Menter and Barker, *Lancet* 338:231, 1991; Barker, *Lancet* 338:227, 1991). It may also be associated with arthritis and can present as a severely inflammatory dermatosis in patients with acquired immunodeficiency syndrome (AIDS) (Duvic, *J. Invest. Dermatol.* 95:385, 1990). The symptoms of psoriasis include sharply defined erythematous patches covered with a distinctive scale, hyperproliferation of the epidermis, incomplete differentiation of keratinocytes and dermal inflammation. Clinical variants of psoriasis include erythroderma, seborrheic, inverse, guttate, and photosensitive psoriasis, pustular variants and Reiter's disease.

The role of immunomodulation in psoriasis is supported by the pharmacological action of drugs such as cyclosporine. For example, inhibition of the synthesis of interleukin-2 prevents the proliferation of T-cells and thus their release of cytokines. Mediators of inflammation play a role in the immunoregulation of psoriasis. Currently available methods for treatment include topical therapy, phototherapy, photochemotherapy and systemic therapy and provide, at best, only temporary relief. Topical glucocorticoids are most commonly prescribed as the initial treatment of psoriasis for their anti-inflammatory, antimitotic and antipruritic effects. However, their efficacy is often short term. Crude coal tar is a complex mixture of thousands of hydrocarbon compounds and affects psoriasis by enzyme inhibition and antimitotic action. Although effective, tar stains the skin and has an odor. Anthralin (dithranol) is used topically and inhibits enzyme metabolism and reduces epidermal mitotic turnover. Remission may last for weeks to months. Phototherapy and photochemotherapy entailing the administration of the photosensitizing drug methoxsalen are only temporarily effective, as psoriasis recurs months after this treatment is discontinued. This recurrence indicates that the therapy is palliative rather than curative. Long-term consequences are altered immunologic effects and an increased risk of carcinogenesis.

Methotrexate is the most commonly administered systemic cytotoxic agent for widespread psoriasis. Contraindications are numerous and after withdrawal, psoriatic symptoms may be more severe than during earlier episodes. Hydroxyurea, etretinate, cyclosporine, and AZT are also systemic medications used for the control of psoriasis and all have serious side effects. Clearly, an understanding of the pathogenesis of psoriasis remains an important challenge in dermatologic medical treatment.

Associations between psoriasis and certain human lymphocyte antigen (HLA) alleles have been described. This factor has been used to support the hypothesis that psoriasis is a T-cell-mediated, autoimmune disorder (Bos, *Br. J. Dermatol.* 118:141, 1988; Baadsgaard et al., *Proc. Nat. Acad. Sci. USA* 87:4256, 1990; Ortonne, *Br. J. Dermatol.* 140:1, 1999). The presence of the HLA-Cw6 allele may predispose to psoriasis because there is a strong association between age of onset, family history, and the presence of HLA-Cw6, B-13 and B-w-57 (Henseler and Christophers, *J. Am. Acad. Dermatol.* 13:450, 1985; Christophers and Henseler, *Acta Dermato-Venereol.* Suppl., 151:88, 1989; Elder et al., *Arch. Dermatol.* 130:216, 1994). The relative risk of HLA-Cw6 carriers developing psoriasis is 20 (Talkainen et al., *Br. J. Dermatol.* 192:179 1980). This association between psoriasis and HLA indicates that certain HLA alleles are more frequent in psoriasis patients than in controls. Loci are "linked" when they do not assort independently at meiosis.

Monozygotic twins have significantly higher concordance rates of disease generally than dizygotic twins (Brandrup et al., *Arch. Dermatol.* 114:874, 1978; Watson et al., *Arch. Dermatol.* 105:197, 1972). Psoriasis has also been reported to aggregate in some families (Pietrzyk et al., *Arch. Dermatol. Res.* 273:295, 1982; Karvonen et al., *Ann. Clin. Res.* 8:298, 1976; Civatte et al., *Ann. Dermatol. Venereol.* 104:525, 1977; Espinoza et al., *J. Rheumatol.* 7:445, 1980). The aggregation of psoriasis in families suggests that psoriasis can be inherited as an autosomal dominant trait with penetrance values of 10 to 50%. About 30% of psoriasis patients have a first degree relative with the disease (Barker, 1991, supra).

A need continues to exist in the medical arts for preparations and techniques for both diagnosing and treating psoriasis and psoriasis-like conditions that have less severe side effects and are more effective in treating the source of the disease. The present invention is directed to compositions, including polynucleotides, polypeptides and antibodies, and methods useful for the diagnosis of psoriasis and/or the amelioration of the symptoms of psoriasis.

SUMMARY OF THE INVENTION

In one aspect, the present invention provides isolated cDNA molecules that encode a CAN-1 polypeptide. An exemplary CAN-1 cDNA of the invention is set forth in SEQ ID NO:1, and encodes the CAN-1 polypeptide set forth in SEQ ID NO:2. The CAN-1 polypeptide of SEQ ID NO:3 is the mature form of the CAN-1 polypeptide of SEQ ID NO:2 and lacks an amino terminal signal sequence. Thus, for example, the present invention encompasses isolated cDNA molecules that encode a CAN-1 polypeptide that is at least 80% identical, at least 90% identical, at least 95% identical or at least 99% identical to a CAN-1 polypeptide consisting of an amino acid sequence set forth in SEQ ID NO:2 or SEQ ID NO:3.

The present invention also encompasses isolated cDNA molecules, that encode a CAN-1 polypeptide, and that are at least 70% (such as at least 80%, at least 90%, at least 95% or at least 99%) identical to the nucleic acid molecule of SEQ ID NO: 1. The present invention also encompasses isolated cDNA molecules that hybridize under conditions of 2×SSC at 55° C. for 30 minutes to the complement of the cDNA molecule set forth in SEQ ID NO:1.

In another aspect, the present invention provides isolated nucleic acid molecules that are at least 70% identical (such as at least 80%, at least 90%, at least 95% or at least 99% identical) to the portion of the CAN-1 cDNA of SEQ ID NO:1 extending from nucleotide 1 through nucleotide 551 of SEQ ID NO:1, or to the complement of the foregoing portion of the cDNA of SEQ ID NO:1.

In one aspect, the present invention provides isolated cDNA molecules and genomic DNA molecules that encode a CAN-1 polypeptide and that include one or more single nucleotide polymorphisms as discussed more fully herein.

In another aspect, the present invention provides isolated genomic DNA molecules that encode a CAN-1 polypeptide, and that are less than 38 kilobases long. Thus, for example, the present invention encompasses isolated genomic DNA molecules that: (a) encode a CAN-1 polypeptide that is at least 80% identical, at least 90% identical, at least 95% identical or at least 99% identical to a CAN-1 polypeptide consisting of an amino acid sequence set forth in SEQ ID NO:2 or SEQ ID NO:3; and (b) are less than 38 kilobases long. Again by way of example, the present invention encompasses isolated genomic DNA molecules that: (a) encode a CAN-1 polypeptide; (b) are less than 38 kilobases long; and (c) hybridize to the complement of the nucleic acid molecule of SEQ ID NO:1 under conditions of 2×SSC at 55° C. for 30 minutes. An exemplary genomic DNA molecule of this aspect of the invention is set forth in SEQ ID NO:4.

In another aspect, the present invention provides isolated oligonucleotides of between 10 base pairs and 100 base pairs that hybridize at 10° C. below their melting temperature (Tm) to the CAN-1 cDNA of SEQ ID NO:1, or to the CAN-1 genomic DNA of SEQ ID NO:4, or to the complement of SEQ ID NO: 1 or SEQ ID NO:4. In a related aspect, the present invention provides isolated oligonucleotides of between 10 base pairs and 100 base pairs that are at least 90% identical to any 10 base pair to 100 base pair portion of the CAN-1 cDNA of SEQ ID NO:1 (such as to any 10 base pair to 100 base pair portion of the portion of SEQ ID NO:1 extending from nucleotide 1 through nucleotide 551), or to any 10 base pair portion of the CAN-1 genomic DNA of SEQ ID NO:4, or to the complement of any 10 base pair portion of SEQ ID NO:1 or SEQ ID NO:4.

In another aspect, the present invention provides isolated nucleic acid molecules (such as isolated nucleic acid molecules that encode an STG protein) that hybridize under conditions of 2×SSC at 55° C. for 30 minutes to the complement of the cDNA molecule set forth in SEQ ID NO:5, provided that the isolated nucleic acid molecule is not a genomic DNA molecule greater than 43 kilobases long. The cDNA molecule set forth in SEQ ID NO:5 encodes the STG protein having the amino acid sequence set forth in SEQ ID NO:6.

In one aspect, the present invention provides isolated cDNA molecules and genomic DNA molecules that encode an STG polypeptide and that include one or more single nucleotide polymorphisms as discussed more fully herein.

In another aspect, the present invention provides isolated oligonucleotides of between 10 base pairs and 100 base pairs that hybridize at 10° C. below their melting temperature (Tm) to the STG cDNA of SEQ ID NO:5, or to the STG genomic clone set forth in SEQ ID NO:7, or to the complement of the STG cDNA of SEQ ID NO:5, or to the complement of the STG genomic clone of SEQ ID NO:7.

The present invention also provides vectors comprising a nucleic acid molecule of the invention (such as a cDNA molecule of the invention), and host cells that include one or more of the vectors of the invention.

The present invention also provides isolated CAN-1 polypeptides that are at least 70% identical (such as at least 80% identical, at least 90% identical, at least 95% identical or at least 99% identical) to the CAN-1 polypeptide of SEQ ID NO:2 or to the CAN-1 polypeptide of SEQ ID NO:3.

The present invention further provides isolated SEEK-1 polypeptides. For example, the SEEK-1 cDNA set forth in SEQ ID NO:8 encodes the SEEK-1 polypeptide set forth in SEQ ID NO:9. Thus, in one aspect, the present invention further provides isolated SEEK-1 polypeptides that are at least 70% identical (such as least 80% identical, at least 90% identical, at least 95% identical, or at least 99% identical) to the SEEK-1 polypeptide of SEQ ID NO:9.

The present invention also provides isolated STG polypeptides. For example, the STG cDNA set forth in SEQ ID NO:5 encodes the STG polypeptide set forth in SEQ ID NO:6. Thus, in one aspect, the present invention further provides isolated STG polypeptides that are at least 70% identical (such as least 80% identical, at least 90% identical, at least 95% identical, or at least 99% identical) to the STG polypeptide of SEQ ID NO:6.

In another aspect, the present invention provides isolated antibodies (such as monoclonal, polyclonal or CDR-grafted antibodies) that bind specifically to a CAN-1, SEEK-1 or STG polypeptide consisting of an amino acid sequence that is at least 70% identical (such as at least 80% identical, at least 90% identical, at least 95% identical or at least 99% identical) to an amino acid sequence selected from the group consisting of SEQ ID NO:2, SEQ ID NO:3, SEQ ID NO:6, and SEQ ID NO:9.

In another aspect, the present invention provides methods of diagnosing or predicting the susceptibility to psoriasis of an individual, the methods each comprising the steps of: (a) obtaining a sample from an individual; (b) determining an expression level of at least one polypeptide chosen from the group consisting of CAN-1, STG and SEEK-1 in the sample; and (c) diagnosing or predicting the susceptibility of the individual to psoriasis based on the presence or amount of the polypeptide.

In another aspect, the present invention provides methods for ameliorating the symptoms and/or progression of psoriasis, the methods comprising administering to an individual suffering from psoriasis an inhibitory amount of a selective inhibitor of at least one polypeptide chosen from the group consisting of CAN-1, STG and SEEK-1, wherein the inhibitory amount causes a reduction in the amount and/or activity of the chosen polypeptide(s). A representative example of a selective inhibitor is an antisense polynucleotide that is complementary to all, or to a portion, of a nucleic acid molecule (such as an mRNA molecule) that encodes a CAN-1, STG or SEEK-1 polypeptide.

In another aspect, the present invention provides methods for making an isolated CAN-1, SEEK-1 or STG polypeptide, the methods each comprising the steps of (a) culturing a host cell, that comprises an expression vector comprising a nucleic acid molecule that encodes a CAN-1, SEEK-1 or STG polypeptide, under conditions that enable expression of the polypeptide; and (b) recovering the expressed polypeptide.

In yet another aspect, the present invention provides methods for identifying a binding partner of a CAN-1, STG or SEEK-1 polypeptide, the methods comprising the steps of (a) contacting a CAN-1, STG or SEEK-1 polypeptide with a binding partner (such as a monoclonal or polyclonal antibody); and (b) determining whether the binding partner affects a biological activity of the polypeptide.

In a further aspect, the present invention provides a method of inhibiting movement of cells into the epidermis comprising contacting a CAN-1 binding partner to a CAN-1 polypeptide such that the binding partner inhibits movement of cells (such as T-cells, endothelial cells, lymphocytes, monocytes and/or neutrophils) into the epidermis by reducing a chemotaxic property of the CAN-1 polypeptide.

The present invention also provides a method of inhibiting hyperproliferation of keratinocytes and/or lymphocytes comprising contacting a CAN-1 binding partner to a CAN-1 polypeptide such that the binding partner inhibits the hyperproliferation of keratinocytes and/or lymphocytes by reducing a hyperproliferation property of the CAN-1 polypeptide.

The present invention also provides a method of inhibiting abnormal differentiation of keratinocytes comprising contacting a CAN-1 binding partner to a CAN-1 polypeptide such that the binding partner inhibits abnormal differentiation of keratinocytes by reducing an amount of unbound CAN-1.

The methods and compositions of the invention are useful, for example, to identify individuals predisposed to psoriasis (but who do not show symptoms of psoriasis), or to identify individuals who are suffering from psoriasis, and/or to ameliorate the symptoms of psoriasis. The methods and compositions of the invention are also useful, for example, to identify agents useful for treating psoriasis (such as CAN-1, SEEK-1 or STG binding partners).

The nucleic acid molecules of the invention are useful, for example, for suppressing the expression of a CAN-1 or STG gene (e.g., by antisense inhibition). Moreover, the nucleic acid molecules of the invention are useful for genetically and/or physically mapping the human genome (such as mapping the location within the human genome of a CAN-1 or STG gene). The polypeptides of the invention are useful, for example, for enhancing the level of CAN-1, STG or SEEK-1 biological activity in a cell or tissue (e.g., by expressing within a cell a nucleic acid molecule encoding a CAN-1, SEEK-1 or STG polypeptide). The antibodies of the invention are useful, for example, for decreasing the level of CAN-1, STG or SEEK-1 biological activity in a cell (e.g., by introducing into a cell, or onto a cell surface, or into sera, an antibody that selectively binds to a CAN-1, SEEK-1 or STG polypeptide).

DETAILED DESCRIPTION OF THE PREFERRED EMBODIMENT

Unless specifically defined herein, all terms used herein have the same meaning as they would to one skilled in the art of the present invention. Practitioners are particularly directed to Sambrook et al. (1989) *Molecular Cloning: A Laboratory Manual,* 2nd ed., Cold Spring Harbor Press, Plainsview, N.Y. (1989), and Ausubel et al., *Current Protocols in Molecular Biology* (Supplement 47), John Wiley & Sons, New York (1999), for definitions and terms of the art.

All references discussed herein are specifically incorporated in their entirety in all respects. U.S. provisional patent application Ser. No. 60/253,592, filed Nov. 28, 2000, and U.S. provisional patent application Ser. No. 60/256,839, filed Dec. 15, 2000, are both incorporated herein by reference in their entirety.

The letter "n" within any nucleic acid sequence set forth herein means that the identity of the nucleic acid residue represented by "n" was not determined and is A, C, G or T.

As used herein, the term "isolated" used with respect to a nucleic acid molecule or polypeptide of the invention means a molecule that is substantially free from cellular components that are associated with the nucleic acid molecule or polypeptide as it is found in nature. As used in this context, the term "substantially free from cellular components" means that the nucleic acid molecule or polypeptide is purified to a purity level of greater than 80% (such as greater than 90%, greater than 95%, or greater than 99%). Moreover, the terms "isolated nucleic acid molecule" and "isolated polypeptide" include nucleic acid molecules and polypeptides which do not naturally occur, and have been produced by synthetic means. An isolated nucleic acid molecule or polypeptide generally resolves as a single, predominant, band by gel electrophoresis, and yields a nucleotide or amino acid sequence profile consistent with the presence of a predominant nucleic acid molecule or polypeptide.

As used herein, the term "CAN-1 polypeptide" refers to a polypeptide that is (a) at least 70% identical to a CAN-1 polypeptide consisting of an amino acid sequence selected from the group consisting of SEQ ID NO:2 and SEQ ID NO:3, (b) has the same biological function as a CAN-1 polypeptide consisting of an amino acid sequence selected from the group consisting of SEQ ID NO:2 and SEQ ID NO:3, and (c) is expressed predominantly or exclusively in human skin.

As used herein, the term "STG polypeptide" refers to a polypeptide that is (a) at least 70% identical to the STG polypeptide of SEQ ID NO:6, and (b) has the same biological function as the STG polypeptide of SEQ ID NO:6.

As used herein, the term "SEEK-1 polypeptide" refers to a polypeptide that is (a) at least 70% identical to the SEEK-1 polypeptide of SEQ ID NO:9, and (b) has the same biological function as the SEEK-1 polypeptide of SEQ ID NO:9.

The term "percent identity" or "percent identical" when used in connection with the nucleic acid molecules and polypeptides of the present invention, is defined as the percentage of nucleic acid residues in a candidate nucleic acid sequence, or the percentage of amino acid residues in a candidate polypeptide sequence, that are identical with a subject nucleic acid sequence or polypeptide molecule sequence (such as the nucleic acid sequence set forth in SEQ ID NO:1, or the polypeptide amino acid sequence set forth in SEQ ID NO:2), after aligning the candidate and subject sequences to achieve the maximum percent identity, and not considering any nucleic acid residue substitutions as part of the nucleic acid sequence identity. When making the comparison, the candidate nucleic acid sequence or polypeptide sequence (which may be a portion of a larger nucleic acid sequence or polypeptide sequence) is the same length as the subject nucleic acid sequence or polypeptide sequence, and no gaps are introduced into the candidate polynucleotide sequence or polypeptide sequence in order to achieve the best alignment.

For example, if a 100 base pair, subject nucleic acid sequence is aligned with a 100 base pair candidate portion of a larger DNA molecule (such as a genomic clone), and 80% of the nucleic acid residues in the 100 base pair candidate portion align with the identical nucleic acid residues in the 100 base pair subject nucleic acid sequence, then the 100 base pair candidate portion of the larger DNA molecule is 80% identical to the subject nucleic acid sequence.

Nucleic acid sequence identity can be determined in the following manner. The subject nucleic acid sequence is used to search a nucleic acid sequence database, such as the GenBank database (accessible at web site http://www.ncbi.nlm.nih.gov/blast/), using the program BLASTM version 2.1 (based on Altschul et al., Nucleic Acids Research 25:3389-3402 (1997)). The program is used in the ungapped mode. Default filtering is used to remove sequence homologies due to regions of low complexity. The default parameters of BLASTM are utilized.

Amino acid sequence identity can be determined in the following manner. The subject polypeptide sequence is used to search a polypeptide sequence database, such as the GenBank database (accessible at web site http://www.ncbi.nlm.nih.gov/blast/), using the BLASTP program. The program is used in the ungapped mode. Default filtering is used to remove sequence homologies due to regions of low complexity. The default parameters of BLASTP are utilized. Filtering for sequences of low complexity utilize the SEG program.

The term "hybridize under stringent conditions", and grammatical equivalents thereof, refers to the ability of a nucleic acid molecule to hybridize to a target nucleic acid molecule (such as a target nucleic acid molecule immobilized on a DNA or RNA blot, such as a Southern blot or Northern blot) under defined conditions of temperature and salt concentration. With respect to nucleic acid molecules greater than about 100 bases in length, typical stringent hybridization conditions are no more than 25° C. to 30° C. (for example, 10° C.) below the melting temperature (Tm) of the native duplex (see generally, Sambrook et al., *Molecular Cloning: A Laboratory Manual*, 2nd Ed. Cold Spring Harbor Press, 1987; Ausubel et al., *Current Protocols in Molecular Biology*, Greene Publishing, 1987). Tm for nucleic acid molecules greater than about 100 bases can be calculated by the formula $Tm=81.5+0.41\% (G+C-\log(Na^+))$.

With respect to nucleic acid molecules having a length less than 100 bases, exemplary stringent hybridization conditions are 5° to 10° C. below Tm.

As used herein, the term "oligonucleotide" refers to a nucleic acid molecule of up to 100 bases.

The term "complement" when used in connection with a nucleic acid molecule refers to the complementary nucleic acid sequence as determined by Watson-Crick base pairing. For example, the complement of the nucleic acid sequence 5'CCATG3' is 5'CATGG3'.

The term "vector" refers to a nucleic acid molecule, usually double-stranded DNA, which may have inserted into it another nucleic acid molecule (the insert nucleic acid molecule) such as, but not limited to, a cDNA molecule. The vector is used to transport the insert nucleic acid molecule into a suitable host cell. A vector that includes the necessary elements that permit transcribing and translating the insert nucleic acid molecule into a polypeptide is called an expression vector. The insert nucleic acid molecule may be derived from the host cell, or may be derived from a different cell or organism. Once in the host cell, the vector can replicate independently of, or coincidental with, the host chromosomal DNA, and several copies of the vector and its inserted nucleic acid molecule may be generated.

The term "functional fragment" when used in reference to a CAN-1 polypeptide refers to a fragment that is a portion of the full-length CAN-1 polypeptide, provided that the portion has a biological activity that is characteristic of the corresponding full-length polypeptide.

The term "functional fragment" when used in reference to a STG polypeptide refers to a fragment that is a portion of the full-length STG polypeptide, provided that the portion has a biological activity that is characteristic of the corresponding full-length polypeptide.

The term "functional fragment" when used in reference to a SEEK-1 polypeptide refers to a fragment that is a portion of the full-length SEEK-1 polypeptide, provided that the portion has a biological activity that is characteristic of the corresponding full-length polypeptide.

The term "antibody" encompasses a whole antibody, or a fragment thereof, for example a F(ab)2, Fab, Fv, VH or VK fragment, a single-chain antibody, a multimeric monospecific antibody or fragment thereof, or a bi- or multispecific antibody or fragment thereof. An antibody according to the invention may be a polyclonal or, especially, a monoclonal antibody. The antibody may belong to any immunoglobulin class, and may be for example an IgG, for example IgG1, IgG2, IgG3, IgG4, IgE, IgM or IgA antibody. It may be of animal, for example mammalian origin, and may be for example a murine, rat or human antibody. Alternatively, the antibody may be a chimeric antibody. The term chimeric antibody is used herein to mean any antibody containing portions derived from different animal species. Particular non-limiting examples include those antibodies having a variable region derived from a murine or other antibody constant region, and those antibodies in which one or more CDR sequences and optionally one or more variable region framework amino acids are derived from a murine or other antibody and the remaining portions of the variable and the constant regions are derived from a human immunoglobulin.

The term "sample" when used in connection with the methods of the invention for diagnosing or predicting the susceptibility to psoriasis in an individual, means any biological fluid, cell, tissue, organ or portion thereof, that includes, or potentially includes, a CAN-1, STG or SEEK-1 nucleic acid molecule or polypeptide. The term includes samples present in an individual as well as samples obtained or derived from an individual. For example, a sample can be a histologic section of a specimen obtained by biopsy, or cells that are placed in or adapted to tissue culture. A sample can be a subcellular fraction or extract, or a purified or crude nucleic acid or polypeptide preparation.

The term "binding partner" when used in reference to CAN-1, STG or SEEK-1 polypeptides, means a composition, such as a macromolecule, that selectively binds a CAN-1, STG or SEEK-1 polypeptide, or fragment thereof. For example, a binding partner can be a monoclonal or polyclonal antibody that selectively binds with high affinity to a CAN-1, STG or SEEK-1 polypeptide, without substantial cross-reactivity with other polypeptides that are unrelated to CAN-1, STG or SEEK-1 polypeptides. The affinity of a binding partner that selectively binds to a CAN-1, STG or SEEK-1 polypeptide is generally greater than about $10^{-5}$M, and more usually greater than about $10^{-6}$M. High affinity interactions are preferred, and are generally greater than about $10^{-8}$M to $10^{-9}$M. Representative examples of binding partners include polyclonal or monoclonal antibodies, peptides, polynucleotides, nucleic acids, nucleic acid derivatives, steroids or steroid analogues, small organic molecules, identified, for example, by affinity screening of a small molecule library.

In one aspect, the present invention provides isolated cDNA molecules that encode a CAN-1 polypeptide. An exemplary CAN-1 cDNA of the invention is set forth in SEQ ID NO:1, and encodes the CAN-1 polypeptide set forth in SEQ ID NO:2. The CAN-1 polypeptide of SEQ ID NO:3 is the mature form of the CAN-1 polypeptide of SEQ ID NO:2 and lacks an amino terminal signal sequence. Thus, for example, the present invention encompasses isolated cDNA molecules that encode a CAN-1 polypeptide that is at least 80% identical, at least 90% identical, at least 95% identical or at least 99% identical to a CAN-1 polypeptide consisting of a nucleic acid sequence set forth in SEQ ID NO:2 or SEQ ID NO:3.

The present invention also encompasses isolated cDNA molecules, that encode a CAN-1 polypeptide, and that are at least 70% (such as at least 80%, at least 90%, at least 95% or at least 99%) identical to the nucleic acid molecule of SEQ ID NO:1. The present invention also encompasses isolated cDNA molecules that hybridize under conditions of 2×SSC at 55° C. for 30 minutes to the complement of the cDNA molecule set forth in SEQ ID NO:1. Some isolated cDNA molecules of this aspect of the invention hybridize under conditions of 1×SSC at 55° C. for 30 minutes to the complement of the cDNA molecule set forth in SEQ ID NO:1. Some isolated cDNA molecules of this aspect of the invention hybridize under conditions of 0.2×SSC at 55° C. for 30 minutes to the complement of the cDNA molecule set forth in SEQ ID NO:1.

In another aspect, the present invention provides isolated nucleic acid molecules that are at least 70% identical (such as at least 80%, at least 90%, at least 95% or at least 99% identical) to the portion of the CAN-1 cDNA of SEQ ID NO:1 extending from nucleotide 1 through nucleotide 551 of SEQ ID NO:1, or to the complement of the foregoing portion of the cDNA of SEQ ID NO:1.

In one aspect, the present invention provides isolated cDNA molecules that encode a CAN-1 polypeptide that is the same length as the CAN-1 polypeptide consisting of the amino acid sequence of SEQ ID NO:2; wherein the encoded CAN-1 polypeptide is at least 70% identical to the CAN-1 polypeptide consisting of the amino acid sequence set forth in SEQ ID NO:2, and wherein the second nucleic acid residue of the codon that encodes the amino acid at position 83 of the CAN-1 polypeptide is T. Some cDNA molecules of this aspect of the invention are the same length as the cDNA molecule set forth in SEQ ID NO:1. Some cDNA molecules of this aspect of the invention encode a CAN-1 polypeptide that has an amino acid sequence that is identical to the amino acid sequence set forth in SEQ ID NO:2 except that the amino acid proline at position 83 of the CAN-1 polypeptide is leucine. An exemplary cDNA molecule of this aspect of the invention has a nucleic acid sequence that is identical to the nucleic acid sequence set forth in SEQ ID NO:1, except that the nucleic acid residue at position 311 of SEQ ID NO:1 is T.

In another aspect, the present invention provides isolated cDNA molecules that encode a CAN-1 polypeptide and are at least 70% identical (such as at least 80% identical, at least 90% identical, at least 95% identical or at least 99% identical) to the CAN-1 cDNA sequence set forth in SEQ ID NO:1, and comprise a thymine (T) residue at position 311. Some isolated cDNA molecules of this aspect of the invention consist of a nucleic acid sequence that is completely identical to the CAN-1 cDNA sequence set forth in SEQ ID NO:1, except that the nucleic acid sequence of the cDNA molecule includes a thymine (T) residue at position 311. Some isolated cDNA molecules of this aspect of the invention hybridize to the complement of the CAN-1 cDNA sequence set forth in SEQ ID NO:1 under conditions of 2×SSC at 55° C. for 30 minutes. Some isolated cDNA molecules of this aspect of the invention hybridize to the complement of the CAN-1 cDNA sequence set forth in SEQ ID NO:1 under conditions of 1×SSC at 55° C. for 30 minutes. Some isolated cDNA molecules of this aspect of the invention hybridize to the complement of the CAN-1 cDNA sequence set forth in SEQ ID NO:1 under conditions of 0.2×SSC at 55° C. for 30 minutes.

In another aspect, the present invention provides isolated genomic DNA molecules that: (a) encode a CAN-1 polypeptide; (b) comprise a nucleic acid sequence that is at least 70% identical (such as at least 80% identical, at least 90% identical, at least 95% identical or at least 99% identical) to the CAN-1 genomic DNA sequence set forth in SEQ ID NO:4; and (c) comprise at least one of the single nucleotide polymorphisms set forth in Table 1 herein. Some isolated genomic DNA molecules of this aspect of the invention comprise a nucleic acid sequence that is completely identical to the CAN-1 genomic DNA sequence set forth in SEQ ID NO:4, except that the nucleic acid sequence of the genomic DNA molecule includes at least one of the single nucleotide polymorphisms set forth in Table 1 herein. Some isolated genomic DNA molecules of this aspect of the invention hybridize to the complement of the CAN-1 genomic DNA sequence set forth in SEQ ID NO:4 under conditions of 2×SSC at 55° C. for 30 minutes. Some isolated genomic DNA molecules of this aspect of the invention hybridize to the complement of the CAN-1 genomic DNA sequence set forth in SEQ ID NO:4 under conditions of 1×SSC at 55° C. for 30 minutes. Some isolated genomic DNA molecules of this aspect of the invention hybridize to the complement of the CAN-1 genomic DNA sequence set forth in SEQ ID NO:4 under conditions of 0.2×SSC at 55° C. for 30 minutes. The exons in the CAN-1 gene consisting of the sequence set forth in SEQ ID NO:4 are located at the following positions: nucleic acid residue 1485 through nucleic acid residue 1539, and nucleic acid residue 2206 through nucleic acid residue 2561.

In another aspect, the present invention provides isolated genomic DNA molecules that encode a CAN-1 polypeptide, and that are less than 38 kilobases long. Thus, for example, the present invention encompasses isolated genomic DNA molecules that: (a) encode a CAN-1 polypeptide that is at least 80% identical, at least 90% identical, at least 95% identical or at least 99% identical to a CAN-1 polypeptide consisting of a nucleic acid sequence set forth in SEQ ID NO:2 or SEQ ID NO:3; and (b) are less than 38 kilobases long. Again by way of example, the present invention encompasses isolated genomic DNA molecules that: (a) encode a CAN-1 polypeptide; (b) are less than 38 kilobases long; and (c) hybridize to the complement of the nucleic acid molecule of SEQ ID NO:1 under conditions of 2×SSC at 55° C. for 30 minutes. Some isolated genomic DNA molecules of this aspect of the invention hybridize under conditions of 1×SSC at 55° C. for 30 minutes to the complement of the cDNA molecule set forth in SEQ ID NO:1. Some isolated genomic DNA molecules of this aspect of the invention hybridize under conditions of 0.2×SSC at 55° C. for 30 minutes to the complement of the cDNA molecule set forth in SEQ ID NO:1.

In another aspect, the present invention provides isolated oligonucleotides of between 10 base pairs and 100 base pairs that hybridize at 110° C. below their melting temperature (Tm) to the CAN-1 cDNA of SEQ ID NO:1, or to the CAN-1 genomic DNA of SEQ ID NO:4, or to the complement of SEQ ID NO:1 or SEQ ID NO:4. In a related aspect, the present invention provides isolated oligonucleotides of between 10 base pairs and 100 base pairs that are at least 90% identical to any 10 base pair portion of the CAN-1 cDNA of SEQ ID NO:1 (such as to any 10 base pair portion of the portion of SEQ ID NO:1 extending from nucleotide 1 through nucleotide 551), or to any 10 base pair portion of the CAN-1 genomic DNA of SEQ ID NO:4, or to the complement of any 10 base pair portion of SEQ ID NO:1 or SEQ ID NO:4.

In another aspect, the present invention provides isolated nucleic acid molecules (such as genomic DNA molecules and cDNA molecules) that hybridize under conditions of 2×SSC at 55° C. for 30 minutes to the complement of the cDNA molecule set forth in SEQ ID NO:5, provided that the isolated nucleic acid molecule is not a genomic DNA molecule greater than 43 kilobases long. The cDNA molecule set forth in SEQ ID NO:5 encodes the STG protein having the amino acid sequence set forth in SEQ ID NO:6. Some isolated nucleic acid molecules of this aspect of the invention hybridize under conditions of 1×SSC at 55° C. for 30 minutes to the complement of the cDNA molecule set forth in SEQ ID NO:5. Some isolated nucleic acid molecules of this aspect of the invention hybridize under conditions of 0.2×SSC at 55° C. for 30 minutes to the complement of the cDNA molecule set forth in SEQ ID NO:5.

In one aspect, the present invention provides isolated cDNA molecules that each: (a) encode an STG polypeptide that is the same length as the STG polypeptide consisting of the amino acid sequence of SEQ ID NO:6, wherein the encoded STG polypeptide is at least 70% identical (such as at least 80% identical, at least 90% identical, at least 95% identical or at least 99% identical) to the STG polypeptide consisting of the amino acid sequence set forth in SEQ ID NO:6; and (b) include at least one of the following single nucleotide polymorphisms: the first nucleic acid residue of the forty eighth codon is A; the second nucleic acid residue of the eighty first codon is C; the first nucleic acid residue of the eighty third codon is C; the third nucleic acid residue of the one hundred and sixty fourth codon is T; the first nucleic acid residue of the one hundred and sixty fifth codon is A; and the third nucleic acid residue of the three hundredth codon is C. Some cDNA molecules of this aspect of the invention are the same length as the cDNA molecule set forth in SEQ ID NO:5.

The present invention also provides isolated cDNA molecules that encode an STG protein and have the same nucleic acid sequence as the cDNA molecule set forth in SEQ ID NO:5, except that each cDNA molecule includes at least one of the following single nucleotide polymorphisms: the nucleic acid residue at position 142 is A; the nucleic acid residue at position 242 is C; the nucleic acid residue at position 247 is C; the nucleic acid residue at position 492 is T; the nucleic acid residue at position 493 is A; the nucleic acid residue at position 900 is C.

The present invention also provides isolated cDNA molecules that encode an STG protein that is at least 70% identical (such as at least 80% identical, at least 90% identical, at least 95% identical or at least 99% identical) to the STG polypeptide consisting of the amino acid sequence set forth in SEQ ID NO:6, except that the STG protein sequence includes at least one of the following amino acid polymorphisms: the amino acid at position 48 is arginine; the amino acid at position 81 is alanine; the amino acid at position 83 is proline; and the amino acid at position 165 is lysine. Some isolated nucleic acid molecules of this aspect of the invention hybridize under conditions of 2×SSC at 55° C. for 30 minutes to the complement of the cDNA molecule set forth in SEQ ID NO:5. Some isolated nucleic acid molecules of this aspect of the invention hybridize under conditions of 1×SSC at 55° C. for 30 minutes to the complement of the cDNA molecule set forth in SEQ ID NO:5. Some isolated nucleic acid molecules of this aspect of the invention hybridize under conditions of 0.2×SSC at 55° C. for 30 minutes to the complement of the cDNA molecule set forth in SEQ ID NO:5.

In another aspect, the present invention provides isolated genomic DNA molecules that: (a) encode an STG polypeptide; (b) comprise a nucleic acid sequence that is at least 70% identical (such as at least 80% identical, at least 90% identical, at least 95% identical or at least 99% identical) to the STG genomic DNA sequence set forth in SEQ ID NO:7; and (c) comprise at least one of the single nucleotide polymorphisms set forth in Table 2 herein. Some isolated genomic DNA molecules of this aspect of the invention comprise a nucleic acid sequence that is completely identical to the STG genomic DNA sequence set forth in SEQ ID NO:7, except that the nucleic acid sequence of the genomic DNA molecule includes at least one of the single nucleotide polymorphisms set forth in Table 2 herein. Some isolated genomic DNA molecules of this aspect of the invention hybridize to the complement of the STG genomic DNA sequence set forth in SEQ ID NO:7 under conditions of 2×SSC at 55° C. for 30 minutes. Some isolated genomic DNA molecules of this aspect of the invention hybridize to the complement of the STG genomic DNA sequence set forth in SEQ ID NO:7 under conditions of 1×SSC at 55° C. for 30 minutes. Some isolated genomic DNA molecules of this aspect of the invention hybridize to the complement of the STG genomic DNA sequence set forth in SEQ ID NO:7 under conditions of 0.2× SSC at 55° C. for 30 minutes. The exons in the STG gene consisting of the sequence set forth in SEQ ID NO:7 are located at the following positions: nucleic acid residue 765 through nucleic acid residue 831, and nucleic acid residue 1029 through nucleic acid residue 1283.

In another aspect, the present invention provides isolated oligonucleotides of between 10 base pairs and 100 base pairs that hybridize at 10° C. below their melting temperature (Tm) to the STG cDNA of SEQ ID NO:5, or to the STG genomic clone set forth in SEQ ID NO:7, or to the complement of the STG cDNA of SEQ ID NO:5, or to the complement of the STG genomic clone of SEQ ID NO:7.

Hybridization can be conducted, for example, by utilizing the technique of hybridizing labeled nucleic acid probes to nucleic acid molecules immobilized on nitrocellulose filters or nylon membranes. An exemplary hybridization protocol is set forth in Example 19 herein. For example, utilizing the exemplary hybridization protocol set forth in Example 19, nucleic acid molecules of the invention, that hybridize under conditions of 2×SSC at 55° C. for 30 minutes to the complement of the nucleic acid molecule consisting of the nucleic acid sequence set forth in SEQ ID NO:1, can be identified by immobilizing the nucleic molecule to a nylon membrane (or nitrocellulose filter). The membrane is incubated in aqueous solution in the presence of the probe nucleic acid molecule (such as the complement of the nucleic acid molecule consisting of the nucleic acid sequence set forth in SEQ ID NO:1) under low stringency conditions (such as 6×SSC at 50° C. for 12 hours). The membrane is then washed under conditions of 2×SSC at 55° C. for 30 minutes. In this example, an isolated nucleic acid molecule of the invention will remain hybridized to the immobilized target molecule under these wash conditions of 2×SSC at 55° C. for 30 minutes.

The nucleic acid molecules of the invention can be isolated by using a variety of cloning techniques known to those of ordinary skill in the art. Thus, for example, all, or portions of, the CAN-1 cDNA of SEQ ID NO:1 can be used as a hybridization probe to screen a genomic or cDNA library, such as a human skin cDNA library. The technique of hybridizing radiolabelled nucleic acid probes to nucleic acids immobilized on nitrocellulose filters or nylon membranes can be used to screen the genomic or cDNA library. Exemplary hybridization and wash conditions are: hybridization at 65° C. in 5.0×SSC, 0.5% sodium dodecyl sulfate, for 12 hours; washing (three washes of twenty minutes each at 55° C.) in 2.0× SSC, 1% (w/v) sodium dodecyl sulfate.

Again, by way of example, nucleic acid molecules of this aspect of the invention can be isolated by the polymerase chain reaction (PCR) described in *The Polymerase Chain Reaction* (K. B. Mullis et al., eds. 1994), incorporated herein by reference. Gobinda et al (*PCR Methods Applic.* 2:318-22 [1993]), incorporated herein by reference, disclose "restriction-site PCR" as a direct method which uses universal primers to retrieve unknown sequence adjacent to a known locus. First, genomic DNA is amplified in the presence of a linker-primer, that is homologous to a linker sequence ligated to the ends of the genomic DNA fragments, and in the presence of a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Further, by way of example, inverse PCR permits acquisition of unknown sequences starting with primers based on a known region (Triglia T. et al., *Nucleic Acids Res* 16:8186 [1988], incorporated herein by reference). The method uses several restriction enzymes to generate a suitable fragment in the known region of a gene. The fragment is then circularized by intramolecular ligation and used as a PCR template. Divergent primers are designed from the known region.

By way of example, the nucleic acid molecules of the invention are useful as hybridization probes in diagnostic procedures (such as diagnosing the presence of psoriasis, or the propensity to develop psoriasis). The particular application and degree of desired specificity will be one consideration well known to those skilled in the art in selecting a probe. Untranslated region sequences are useful regions to construct probes since there is little evolutionary pressure to conserve non-coding domains.

Hybridization probes can be produced recombinantly or chemically synthesized using methods well known in the art. Additionally, hybridization probes can be labeled with a variety of detectable labels including, for example, radioisotopes, fluorescent tags, reporter enzymes, biotin and other ligands. Such detectable labels can additionally be coupled with, for example, calorimetric or photometric indicator substrate for spectrophotometric detection. Methods for labeling and detecting such probes are well known in the art and can be found described in, for example, Sambrook et al., supra, and Ausubel et al., supra.

In another aspect, the present invention is directed to regulatory nucleic acid sequences that are operably linked to a CAN-1 gene, an STG gene, or to a SEEK-1 gene. The term "regulatory nucleic acid sequence" refers to nucleic acid sequences located upstream, within, or downstream of a coding sequence, and which influence the transcription, RNA processing or stability, or translation of the associated coding sequence. Regulatory sequences include, but are not limited to, enhancers, promoters, translation leader sequences, introns, and polyadenylation signal sequences.

"Promoter" refers to a DNA sequence involved in controlling the expression of a coding sequence or functional RNA. In general, a coding sequence is located 3' to a promoter sequence. The term "promoter" includes a minimal promoter that is a short DNA sequence comprised of a TATA-box and other sequences that serve to specify the site of transcription initiation, to which other regulatory elements may be added for control of expression. "Promoter" also refers to a nucleic acid sequence that includes a minimal promoter plus other regulatory elements that are capable of controlling the expression of a coding sequence or functional RNA. This type of promoter sequence typically consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

In another aspect, the invention provides vectors that comprise a nucleic acid molecule of the invention. Some vectors of the invention include a nucleic acid molecule that encodes a CAN-1 polypeptide that is at least 80% identical, at least 90% identical, at least 95% identical or at least 99% identical, to a CAN-1 polypeptide consisting of a nucleic acid sequence set forth in SEQ ID NO:2 or SEQ ID NO:3.

Some vectors of the invention include a nucleic acid molecule that encodes a CAN-1 polypeptide, and that is at least 70% (such as at least 80%, at least 90%, at least 95% or at least 99%) identical to the nucleic acid molecule of SEQ ID NO:1. Some vectors of the invention include a nucleic acid molecule that encodes a CAN-1 polypeptide, and that hybridizes under conditions of 2×SSC at 55° C. for 30 minutes to the complement of the cDNA molecule set forth in SEQ ID NO:1. Some vectors of the invention include a nucleic acid molecule that encodes a CAN-1 polypeptide, and that hybridizes under conditions of 1×SSC at 55° C. for 30 minutes to the complement of the cDNA molecule set forth in SEQ ID NO:1. Some vectors of the invention include a nucleic acid molecule that encodes a CAN-1 polypeptide, and that hybridizes under conditions of 0.2×SSC at 55° C. for 30 minutes to the complement of the cDNA molecule set forth in SEQ ID NO:1.

Some vectors of the invention include a nucleic acid molecule that encodes an STG polypeptide, and that is at least 70% (such as at least 80%, at least 90%, at least 95% or at least 99%) identical to the nucleic acid molecule of SEQ ID NO:5. Some vectors of the invention include a nucleic acid molecule that encodes an STG polypeptide, and that hybridizes under conditions of 2×SSC at 55° C. for 30 minutes to the complement of the cDNA molecule set forth in SEQ ID NO:5. Some vectors of the invention include a nucleic acid molecule that encodes an STG polypeptide, and that hybridizes under conditions of 1×SSC at 55° C. for 30 minutes to the complement of the cDNA molecule set forth in SEQ ID NO: 5. Some vectors of the invention include a nucleic acid molecule that encodes an STG polypeptide, and that hybridizes under conditions of 0.2×SSC at 55° C. for 30 minutes to the complement of the cDNA molecule set forth in SEQ ID NO:5.

The vectors are constructed using conventional techniques well known to those skilled in the art. The choice of vector is dependent, for example, upon the method that would be used to transform the host cells and the desired selection markers. The skilled artisan is well aware of the genetic elements that can be included on the vector in order to successfully transform, select and propagate host cells containing the vector. For example, a vector may also include any other necessary regulatory sequences such as terminators (Guerineau et al., *Mol. Gen. Genet.* 226:141-144 [1991]; Proudfoot, *Cell* 64:671-674 [1991]; Sanfacon et al., *Genes & Dev.* 5:141-149 [1991]; Mogen et al., *Plant Cell* 2:1261-1272 [1990]; Munroe et al., *Gene* 91:151-158 [1990]; Ballas et al., *Nucleic Acids Res.* 17:7891-7903 [1989]; Joshi et al., *Nucleic Acid Res.* 15:9627-9639 [1987]); nuclear localization signals (Kalderon et al., *Cell* 39:499-509 [1984]; Lassner et al., *Plant Mol. Biol.* 17:229-234 [1991]); introns (Luehrsen & Walbot, *Mol. Gen. Genet.,* 225:81-93 [1991]) and the like, operably linked to the nucleotide sequence encoding the transactivator and/or the toxic product. It may also be beneficial to include 5' leader sequences. Such leader sequences can act to enhance translation. Translational leaders are known in the art and include Picornavirus leaders, for example, Encephalomyocarditis leader (Elroy-Stein et al., *Proc. Natl. Acad. Sci. USA* 86:6126-6130 [1989]).

In another aspect, the present invention is directed to isolated CAN-1, SEEK-1 and STG polypeptides. The polypeptides of the present invention can be isolated, for example, by incorporating a nucleic acid molecule encoding the polypeptide into an expression vector, introducing the expression vector into a host cell and expressing the nucleic acid molecule to yield polypeptide. The polypeptide can then be purified by art-recognized means. When a crude polypeptide extract is initially prepared, it may be desirable to include one or more protease inhibitors in the extract. Representative examples of protease inhibitors include: serine protease inhibitors (such as phenylmethylsulfonyl fluoride (PMSF), benzamide, benzamidine HCl, ε-Amino-n-caproic acid and aprotinin (Trasylol); cysteine protease inhibitors, such as sodium p-hydroxymercuribenzoate; competitive protease inhibitors, such as antipain and leupeptin; covalent protease inhibitors, such as iodoacetate and N-ethylmaleimide; aspartate (acidic) protease inhibitors, such as pepstatin and diazoacetylnorleucine methyl ester (DAN); metalloprotease inhibitors, such as EGTA [ethylene glycol bis(β-aminoethyl ether) N,N,N',N'-tetraacetic acid], and the chelator 1,10-phenanthroline.

Fusion polypeptides may also be engineered to improve characteristics of the inventive polypeptides. For instance, a region of additional amino acids, particularly charged amino acids, may be added to the N-terminus of the polypeptide to improve stability and persistence during purification from a host cell, or during subsequent storage and handling. Such regions may be removed prior to final preparation of the polypeptide. The addition of peptide moieties to facilitate handling of polypeptides are familiar and routine techniques in the art. For example, a hexa-histidine peptide, such as the tag provided in a pOE vector (Qiagen, Inc., Chatsworth, Calif.), among others, many of which are commercially available, can be used to facilitate purification of inventive fusion polypeptides. Gentz et al. (*Proc. Natl. Acad. Sci. USA* 86:821, 1989) also discloses the use of another peptide tag, "HA", which corresponds to an epitope derived from the influenza hemagglutinin polypeptide (Wilson, *Cell* 37:767, 1984).

Thus, any of the above mentioned fusion polypeptides can be engineered using the polynucleotides or the polypeptides of the present invention.

Moreover, polypeptides of the invention, including fragments, and specifically epitopes, can be combined with parts of the constant domain of immunoglobulins (IgG), resulting in fusion polypeptides. This class of fusion polypeptide usually facilitate purification and show an increased half-life in vivo. One reported example, describes chimeric polypeptides consisting of the first two domains of the human CD4-polypeptide and various domains of the constant regions of the heavy or light chains of mammalian immunoglobulins (EP A 394,827; Traunecker et al., *Nature* 331:84, 1988). Fusion polypeptides having disulfide-linked dimeric structures (due to the IgG) can also be more efficient in binding and neutralizing other molecules, than the monomeric secreted polypeptide or polypeptide fragment alone (Fountoulakis et al., *J. Biochem.* 270:3958, 1995).

Similarly, EP A 0464533 (Canadian counterpart 2045869) discloses fusion polypeptides comprising various portions of a constant region of immunoglobulin molecules together with another human polypeptide or part thereof. In many cases, the Fc part in a fusion polypeptide is beneficial in therapy and diagnosis, and thus can result in, for example, improved pharmocokinetic properties (EP A 0232262). Alternatively, deleting the Fc part after the fusion polypeptide has been expressed, detected, and purified, would be desired. For example, the Fc portion may hinder therapy and diagnosis if the fusion polypeptide is used as an antigen for immunizations. In drug discovery, for example, human polypeptides, such as hIL-5, have been fused with Fc portions for the purpose of high-throughput screening assays to identify antagonists of hIL-5 (see, Bennett et al., *J. Molecular Recognition* 8:52, 1995; Johanson et al., *J. Biol. Chem.* 270:9459, 1995).

In another aspect, the present invention provides nucleic acid and amino acid polymorphisms of the CAN-1, SEEK-1 and STG nucleic acid molecules and polypeptides of the invention. By way of example, nucleic acid polymorphisms of the invention can be identified by using a CAN-1, SEEK-1 or STG cDNA as a probe to screen a mammalian genomic library to identify polymorphic CAN-1, SEEK-1 and/or STG genes. Exemplary nucleic acid polymorphisms of the invention are set forth in Tables 1, 2 and 3 herein.

In another aspect, the present invention is directed to antibodies that bind specifically to polypeptides of the invention, and/or to fragments thereof. By way of representative example, antigen useful for raising antibodies can be prepared in the following manner. A nucleic acid molecule (such as a cDNA molecule) encoding a CAN-1, SEEK-1 or STG polypeptide is cloned into a plasmid vector, such as a Bluescript plasmid (available from Stratagene, Inc., La Jolla, Calif.). The recombinant vector is then introduced into an *E. coli* strain (such as *E. coli* XL1-Blue, also available from Stratagene, Inc.) and the polypeptide encoded by the nucleic acid molecule is expressed in *E. coli* and then purified. For example, *E. coli* XL1-Blue harboring a Bluescript vector including a cDNA molecule of interest is grown overnight at 37° C. in LB medium containing 100 μg ampicillin/ml. A 50 μl aliquot of the overnight culture is used to inoculate 5 ml of fresh LB medium containing ampicillin, and the culture grown at 37° C. with vigorous agitation to $A_{600}$=0.5 before induction with 1 mM IPTG. After an additional two hours of growth, the suspension is centrifuged (1000×g, 15 min, 4° C.), the media removed, and the pelleted cells resuspended in 1 ml of cold buffer that preferably contains 1 mM EDTA and one or more polypeptidease inhibitors, such as those described herein in connection with the purification of the isolated polypeptides of the present invention. The cells can be disrupted by sonication with a microprobe. The chilled sonicate is cleared by centrifugation and the expressed, recombinant polypeptide purified from the supernatant by art-recognized polypeptide purification techniques, such as those described herein.

Inventive polypeptides can also be prepared using peptide synthesis methods that are well known in the art. The synthetic polypeptides can then be used to prepare antibodies. Direct peptide synthesis using solid-phase techniques (Stewart et al., Solid-Phase Peptide Synthesis, W H Freeman Co, San Francisco Calif. (1969); Merrifield, *J. Am. Chem. Soc.* 85:2149-2154 (1963) is an alternative to recombinant or chimeric peptide production. Automated synthesis may be achieved, for example, using Applied Biosystems 431A Peptide Synthesizer (Foster City, Calif.) in accordance with the instructions provided by the manufacturer. Additionally the polypeptide sequences of the present invention or any fragment thereof may be mutated during direct synthesis and, if desired, combined using chemical methods with other amino acid sequences. The polypeptides used to induce specific antibodies may have an amino acid sequence consisting of at least five amino acids and preferably at least 10 amino acids. Short stretches of amino acid sequence may be attached with those of another polypeptide, and the chimeric polypeptide used for antibody production. Alternatively, the polypeptide may be of sufficient length to contain an entire domain for antibody recognition.

Representative examples of art-recognized techniques for purifying, or partially purifying, polypeptides from biological material are exclusion chromatography, ion-exchange chromatography, hydrophobic interaction chromatography, reversed-phase chromatography and immobilized metal affinity chromatography.

Hydrophobic interaction chromatography and reversed-phase chromatography are two separation methods based on the interactions between the hydrophobic moieties of a sample and an insoluble, immobilized hydrophobic group present on the chromatography matrix. In hydrophobic interaction chromatography the matrix is hydrophilic and is substituted with short-chain phenyl or octyl nonpolar groups. The mobile phase is usually an aqueous salt solution. In reversed phase chromatography the matrix is silica that has been substituted with longer n-alkyl chains, usually $C_8$ (octyl-silyl) or $C_{18}$ (octadecylsilyl). The matrix is less polar than the mobile phase. The mobile phase is usually a mixture of water and a less polar organic modifier.

Separations on hydrophobic interaction chromatography matrices are usually done in aqueous salt solutions, which generally are nondenaturing conditions. Samples are loaded onto the matrix in a high-salt buffer and elution is by a descending salt gradient. Separations on reversed-phase media are usually done in mixtures of aqueous and organic solvents, which are often denaturing conditions. In the case of polypeptide and/or peptide purification, hydrophobic interaction chromatography depends on surface hydrophobic groups and is carried out under conditions which maintain the integrity of the polypeptide molecule. Reversed-phase chromatography depends on the native hydrophobicity of the polypeptide and is carried out under conditions which expose nearly all hydrophobic groups to the matrix, i.e., denaturing conditions.

Ion-exchange chromatography is designed specifically for the separation of ionic or ionizable compounds. The stationary phase (column matrix material) carries ionizable functional groups, fixed by chemical bonding to the stationary phase. These fixed charges carry a counterion of opposite sign. This counterion is not fixed and can be displaced. Ion-exchange chromatography is named on the basis of the sign of the displaceable charges. Thus, in anion ion-exchange chromatography the fixed charges are positive and in cation ion-exchange chromatography the fixed charges are negative.

Retention of a molecule on an ion-exchange chromatography column involves an electrostatic interaction between the fixed charges and those of the molecule, binding involves replacement of the nonfixed ions by the molecule. Elution, in turn, involves displacement of the molecule from the fixed charges by a new counterion with a greater affinity for the fixed charges than the molecule, and which then becomes the new, nonfixed ion.

The ability of counterions (salts) to displace molecules bound to fixed charges is a function of the difference in affinities between the fixed charges and the nonfixed charges of both the molecule and the salt. Affinities in turn are affected by several variables, including the magnitude of the net charge of the molecule and the concentration and type of salt used for displacement.

Solid-phase packings used in ion-exchange chromatography include cellulose, dextrans, agarose, and polystyrene. The exchange groups used include DEAE (diethylaminoethyl), a weak base, that will have a net positive charge when ionized and will therefore bind and exchange anions; and CM (carboxymethyl), a weak acid, with a negative charge when ionized that will bind and exchange cations. Another form of weak anion exchanger contains the PEI (polyethyleneimine) functional group. This material, most usually found on thin layer sheets, is useful for binding polypeptides at pH values above their pI. The polystyrene matrix can be obtained with quaternary ammonium functional groups for strong base anion exchange or with sulfonic acid functional groups for strong acid cation exchange. Intermediate and weak ion-exchange materials are also available. Ion-exchange chromatography need not be performed using a column, and can be performed as batch ion-exchange chromatography with the slurry of the stationary phase in a vessel such as a beaker.

Gel filtration is performed using porous beads as the chromatographic support. A column constructed from such beads will have two measurable liquid volumes, the external volume, consisting of the liquid between the beads, and the internal volume, consisting of the liquid within the pores of the beads. Large molecules will equilibrate only with the external volume while small molecules will equilibrate with both the external and internal volumes. A mixture of molecules (such as polypeptides) is applied in a discrete volume or zone at the top of a gel filtration column and allowed to percolate through the column. The large molecules are excluded from the internal volume and therefore emerge first from the column while the smaller molecules, which can access the internal volume, emerge later. The volume of a conventional matrix used for polypeptide purification is typically 30 to 100 times the volume of the sample to be fractionated. The absorbance of the column effluent can be continuously monitored at a desired wavelength using a flow monitor.

A technique that is often applied to the purification of polypeptides is High Performance Liquid Chromatography (HPLC). HPLC is an advancement in both the operational theory and fabrication of traditional chromatographic systems. HPLC systems for the separation of biological macromolecules vary from the traditional column chromatographic systems in three ways; (1) the column packing materials are of much greater mechanical strength, (2) the particle size of the column packing materials has been decreased 5- to 10-fold to enhance adsorption-desorption kinetics and diminish bandspreading, and (3) the columns are operated at 10-60 times higher mobile-phase velocity. Thus, by way of non-limiting example, HPLC can utilize exclusion chromatography, ion-exchange chromatography, hydrophobic interaction chromatography, reversed-phase chromatography and immobilized metal affinity chromatography. Art-recognized techniques for the purification of polypeptides and peptides are set forth in Methods in Enzymology, Vol. 182, Guide to Polypeptide Purification, Murray P. Deutscher, ed (1990).

Methods for preparing monoclonal and polyclonal antibodies are well known to those of ordinary skill in the art and are set forth, for example, in chapters five and six of *Antibodies A Laboratory Manual*, E. Harlow and D. Lane, Cold Spring Harbor Laboratory (1988). For example, antibodies according to the invention may be prepared by conventional immunization and recombinant DNA techniques. Thus, for example polyclonal antibodies may be obtained from the sera of animals immunised with a CAN-1, SEEK-1 or STG protein or fragment thereof. Any suitable host, for example BALB/c mice where it is desired to obtain a mouse polyclonal antibody, may be injected with the immunogen, the serum collected and the antibody recovered therefrom. Monoclonal antibodies may be obtained from hybridomas derived form the spleen cells of an animal immunised as just discussed and fused to an appropriate "immortal" B-tumour cell. In each instance, the antibody may be recovered from either the serum or the hybridoma by making use of standard purification and or concentration techniques, for example by chromatography, using for example Protein A or by other affinity chromatography employing a protein of the invention or fragment thereof.

Once a cell line, for example a hybridoma, expressing an antibody according to the invention has been obtained it is possible to clone therefrom the cDNA and to identify the variable region genes encoding the desired antibody, including the sequences encoding the CDRs. From here, other chimeric antibodies according to the invention may be obtained by preparing one or more replicable expression vectors containing at least the DNA sequence encoding the variable domain of the antibody heavy or light chain and optionally other DNA sequences encoding remaining portions of the heavy and/or light chains as desired, and transforming an appropriate cell line, e.g., a non-producing myeloma cell line, such as a mouse NSO line, in which production of the antibody will occur. In order to obtain efficient transcription and translation, the DNA sequence in each vector should include appropriate regulatory sequences, particularly a promoter and leader sequence operably linked to the variable domain sequence. Particular methods for producing antibodies in this way are generally well known and routinely used. For example, basic molecular biology procedures are described by Maniatis et al (Molecular Cloning, Cold Spring Harbor Laboratory, New York, 1989); DNA sequencing can be performed as described in Sanger et al (*PNAS* 74: 5463, (1977)) and the Amersham International plc sequencing handbook; and site directed mutagenesis can be carried out according to the method of Kramer et al (*Nucl. Acids Res.* 12: 9441, (1984)) and the Anglian Biotechnology Ltd. handbook. Additionally, there are numerous publications, including patent specifications, detailing techniques suitable for the preparation of antibodies by manipulation of DNA, creation of expression vectors and transformation of appropriate cells, for example as reviewed by Mountain A and Adair, J R in Biotechnology and Genetic Engineering Reviews [ed. Tombs, M P, 10, Chapter 1, 1992, Intercept, Andover, UK] and in International Patent Specification No. WO 91/09967.

Antibody production includes not only the stimulation of an immune response by injection into animals, but also analogous processes such as the production of synthetic antibodies, the screening of recombinant immunoglobulin libraries for specific-binding molecules (Orlandi et al., *Proc. Natl. Acad. Sci. USA* 86:3833, 1989, or Huse et al. *Science* 256:1275, 1989), or the in vitro stimulation of lymphocyte populations.

Current technology (Winter and Milstein, *Nature* 349:293, 1991) provides for a number of highly specific binding reagents based on the principles of antibody formation. These techniques may be adapted to produce molecules which specifically bind to the inventive polypeptides or fragments thereof. Antibodies or other appropriate molecules generated against a specific immunogenic peptide fragment or polypeptide can be used in Western analysis, enzyme-linked immunosorbent assays (ELISA) or similar tests to establish the presence of, or to quantitate amounts of, any one the inventive polypeptides in normal, diseased, or therapeutically treated cells or tissues. Variations on any procedure known in the art for the measurement of polypeptides can be used in the practice of the instant invention. Such procedures include but are not limited to competitive and non-competitive assay systems using techniques such as radioimmunoassays, ELISA (enzyme linked immunoabsorbent assay), sandwich immunoassays, agglutination assays, complement fixation assays, immunoradiometric assays, fluorescent immunoassays, polypeptide A immunoassays, immunoelectrophoresis assays and the like.

In another aspect, the present invention provides methods of diagnosing or predicting the susceptibility to psoriasis of an individual, the methods each comprising the steps of: (a) obtaining a sample from an individual; (b) determining an expression level of at least one polypeptide chosen from the group consisting of CAN-1, STG and SEEK-1 in the sample; and (c) diagnosing or predicting the susceptibility of the individual to psoriasis based on the presence or amount of the polypeptide. In some embodiments of the method of this aspect of the invention, step (b) comprises determining an expression level of a CAN-1 polypeptide in said sample, wherein the CAN-1 polypeptide is at least 70% (such as at least 80%, at least 90%, at least 95% or at least 99%) identical to the CAN-1 polypeptide of either SEQ ID NO:2 or SEQ ID NO:3. In some embodiments of the method of this aspect of the invention, step (b) comprises determining an expression level of an STG polypeptide in said sample, wherein the STG polypeptide is at least 70% (such as at least 80%, at least 90%, at least 95% or at least 99%) identical to the STG polypeptide of SEQ ID NO:6. In some embodiments of the method of this aspect of the invention, step (b) comprises determining an expression level of a SEEK-1 polypeptide in said sample, wherein the SEEK-1 polypeptide is at least 70% (such as at least 80%, at least 90%, at least 95% or at least 99%) identical to the SEEK-1 polypeptide of SEQ ID NO:9.

Thus, in one embodiment, an individual is diagnosed as being susceptible to, or suffering from, psoriasis by virtue of a level of CAN-1, SEEK-1 and/or STG that is at least two-fold higher than a control level measured in a population of individuals who are not susceptible to psoriasis, and/or who do not suffer from psoriasis.

The methods of this aspect of the invention are applicable for use with a variety of different types of samples isolated or obtained from an individual. For example, tissue samples and/or cell samples can be used. A tissue or cell sample can be obtained, for example, by biopsy or surgery. As described below, and depending on the format of the method, the tissue can be used whole or subjected to various methods known in the art to disassociate the sample into smaller pieces, cell aggregates or individual cells. Additionally, when combined with amplification methods such as polymerase chain reaction (PCR), a single skin cell sample is sufficient for use in diagnostic assays of the invention which employ nucleic acid hybridization detection methods. Similarly, when measuring polypeptide levels or activity levels, amplification of the signal with enzymatic coupling or photometric enhancement can be employed using only a few or a small number of cells.

Whole tissue obtained from a skin biopsy or surgery is one example of a skin cell sample. Whole tissue skin samples can be assayed employing any of the formats described below. For example, the skin tissue sample can be mounted and hybridized in situ with a nucleic acid probe of the present invention. Similar histological formats employing polypeptide detection methods and in situ activity assays also can be used to detect polypeptides of the invention in whole skin tissue cell samples. Polypeptide detection methods include, for example, staining with antibodies specific for a target polypeptide (e.g., CAN-1) and activity assays which result in the deposition of a polypeptide end product at the site of enzyme activity in the sample. Such histological methods as well as others are well known to those skilled in the art and are applicable for use in the diagnostic methods of the invention using whole tissue as the source of the sample. Methods for preparing and mounting the samples are similarly well known in the art.

Individual keratinocyte cells and cell aggregates from an individual having, or suspected of having, psoriasis is another example of a skin cell sample which can be analyzed for increased or decreased expression of CAN-1, SEEK-1 or STG polypeptide or activity. The cells can be grown in culture and analyzed in situ using procedures such as those described above. The expression level can be determined by, for example, binding agents specific for CAN-1, SEEK-1 or STG polypeptides, or by hybridization to a probe specific to at least 15 contiguous nucleotides of a nucleic acid molecule encoding a CAN-1, SEEK-1 or STG polypeptide. Other methods for measuring the expression level of the inventive polypeptides or polynucleotides in whole cell samples are known in the art and are similarly applicable in any of the diagnostic formats described below.

The sample obtained from an individual also can be analyzed for increased or decreased expression of CAN-1, SEEK-1 and/or STG by lysing the cell and measuring the expression levels of CAN-1, SEEK-1 or STG polypeptide or nucleic acid molecule in the lysate, a fractionated portion thereof, or a purified component thereof using any of diagnostic formats described below. For example, if a hybridization format is used, RNA from one or more of the inventive polynucleotides can be amplified directly from the lysate using PCR, or other amplification procedures well known in the art such as RT-PCR, 5' or 3' RACE to directly measure the expression levels of CAN-1, SEEK-1 or STG. RNA also can be isolated and probed directly such as by solution hybridization or indirectly by hybridization to immobilized RNA. Similarly, when determining the expression level of the polypeptides of the invention using polypeptide detection or enzyme activity formats, lysates can be assayed directly, or they can be further fractionated to enrich for the inventive polypeptides and their corresponding activities. Numerous other methods applicable for use with various cell fractions are well known to those skilled in the art and can accordingly be used in the methods of the invention.

The sample (such as a skin sample) can be obtained directly from the individual or, alternatively, it can be obtained from other sources for testing. Similarly, the sample can be tested when it is freshly isolated or it can be tested following short or prolonged periods of cryopreservation without substantial loss in accuracy or sensitivity. If the sample is to be tested following an indeterminate period of time, it can be obtained and then cryopreserved, or stored at 4° C. for short periods of time, for example. An advantage of the diagnostic methods of the invention is that they do not require histological analysis of the sample. As such, the sample can be initially disaggregated, lysed, fractionated or purified and the active component stored for later diagnosis.

The diagnostic methods of the invention are applicable for use with a variety of different types of samples other than skin cell samples. For example, intracellular nucleic acid molecules and polypeptides of the invention may leak into the extracellular space when a psoriatic condition causes a disruption of the normal skin architecture. Therefore, the diagnostic methods of the invention are applicable with fluid samples collected from an individual having, or suspected of having psoriasis.

Fluid samples which can be measured for CAN-1, SEEK-1 or STG expression levels include, for example, blood, serum, lymph, urine and semen. Other bodily fluids are known to those skilled in the art and are similarly applicable for use as a sample in the diagnostic methods of the invention. One advantage of analyzing fluid samples is that they are readily obtainable, in sufficient quantity, without invasive procedures as required by biopsy and surgery. Analysis of fluid samples such as blood, serum and urine will generally be in the diagnostic formats described above and below which measure CAN-1, SEEK-1 and/or STG polypeptide levels or activity. As the inventive polypeptides are circulating in bodily fluids, the methods will be similar to those which measure expression levels from cell lysates, fractionated portions thereof or purified components.

Psoriasis can be diagnosed, predicted or prognosed by measuring the expression levels of the nucleic acid molecules and polypeptides of the present invention in a tissue or cell sample, circulating fluid, or other bodily fluid obtained from the individual. As described above, expression levels can be measured by a variety methods known in the art. For example, the expression level of a nucleic acid of the invention can be determined by measuring the amount of an RNA or polypeptide of the invention in a sample from the individual. Alternatively, the expression level of the inventive polypeptides can be determined by measuring the amount of enzyme activity in the sample, the amount of activity being indicative of the expression level of the inventive polynucleotide.

Given the teachings and guidance provided herein, the choice of measuring nucleic acid (such as RNA), polypeptide or activity will be that of the user. Considerations such as the sample type, availability and amount will also influence selection of a particular diagnostic format. For example, if the sample is a kaeratinocyte cell sample and there is only a small amount available, then diagnostic formats which measure the amount of RNA by, for example, PCR amplification, can be an appropriate choice for determining the expression level of a nucleic acid molecule of the invention. Alternatively, if the sample is a blood sample and the user is analyzing numerous different samples simultaneously, such as in a clinical setting, then a multi sample format, such as an Enzyme Linked Immunoabsorbent Assay (ELISA), which measures the amount of polypeptide can be an appropriate choice for determining the expression level of a polypeptide of the invention. Additionally, nucleic acid molecules of the invention released into bodily fluids from psoriatic skin cells can also be analyzed by, for example, PCR or RT-PCR. Those skilled in the art will know, or can determine which format is amenable for a particular application and which methods or modifications known within the art are compatible with a particular type of format.

Hybridization methods are applicable for measuring the amount of RNA as an indicator of expression levels. There are numerous methods well known in the art for detecting nucleic acid molecules by specific or selective hybridization with a complementary probe. Such methods include both solution hybridization procedures and solid-phase hybridization procedures where the probe or sample is immobilized to a solid support. Descriptions for such methods can be found in, for example, Sambrook et al., supra, and in Ausubel et al., supra. Specific examples of such methods include PCR and other amplification methods such as RT-PCR, 5' or 3' RACE, RNase protection, RNA blot, dot blot or other membrane-based technologies, dip stick, pin, ELISA or two-dimensional arrays immobilized onto chips as a solid support. These methods can be performed using either qualitative or quantitative measurements, all of which are well known to those skilled in the art.

PCR or RT-PCR can be used with isolated RNA or crude cell lysate preparations. As described previously, PCR is advantageous when there is little starting material. A further description of PCR methods can be found in, for example, Dieffenbach, C. W., and Dveksler, G. S., *PCR Primer: A Laboratory Manual*, Cold Spring Harbor Press, Plainsview, N.Y. (1995). Multi sample formats such as an ELISA or two-dimensional array offer the advantage of analyzing numerous, different samples in a single assay. A particular example of a two-dimensional array used in a hybridization format is described further below in the Examples. In contrast, solid-phase dip stick-based methods offer the advantage of being able to rapidly analyze a patient's fluid sample and obtain an immediate result.

Polynucleotide probes useful for measuring the expression level of the nucleic acid molecules of the invention by hybridization include, for example, all of the inventive nucleic acid molecules described herein.

Briefly, for detection by hybridization, one or more polynucleotide probes having detectable labels are added to a cell, tissue or fluid sample obtained from an individual under conditions which allow annealing of the probe to RNA. Such conditions are well known in the art for both solution and solid phase hybridization procedures. Moreover, optimization of hybridization conditions can be performed, if desired, by hybridization of an aliquot of the sample at different temperatures, durations and in different buffer conditions. Such procedures are routine and well known to those skilled. Following annealing, the sample is washed and the signal is measured and compared with a suitable control or standard value. The magnitude of the hybridization signal is directly proportional to the expression levels of the polynucleotide of the invention for which the probe was specific.

A suitable control for comparison can be, for example, the expression level of a nucleic acid molecule of the invention from a skin cell or a fluid sample obtained from a normal individual. The control sample for comparison can be measured simultaneously with one or more test samples or, alternatively, expression levels can be established for a particular type of sample and standardized to internal or external parameters such as polypeptide or polynucleotide content, cell number or mass of tissue. Such standardized control samples can then be directly compared with results obtained from the test sample. An increase (such as, by way of non-limiting example, an increase of two-fold or more) of expression levels of a nucleic acid molecule of the invention indicates the presence psoriasis in the tested individual.

The diagnostic procedures described above and below using the inventive nucleic acid molecule and polypeptide probes can additionally be used in conjunction with other psoriasis markers, for simultaneous or independent corroboration of a sample. Those skilled in the art will know which markers are applicable for use in conjunction with a nucleic acid molecule or polypeptide of the invention to delineate more specific diagnostic information such as that described above.

Therefore, in one aspect, the invention provides a method of diagnosing or predicting the susceptibility of a psoriatic condition in an individual suspected of having psoriasis where the expression level of a nucleic acid molecule of the invention is determined by measuring the amount of its respective RNA. The amount of CAN-1, STG or SEEK-1 RNA can be determined by hybridization with a polynucleotide probe of at least 10 nucleotides in length.

The invention additionally provides a method of diagnosing or predicting the susceptibility of a psoriatic condition in an individual suspected of having psoriasis where the expression level of an inventive polypeptide is determined by measuring the amount of polypeptide. The method comprises contacting a cell or tissue sample, or lysate thereof, or fractionated sample thereof, from an individual suspected of having psoriasis with a binding agent selective for one of the inventive polypeptides, and determining the amount of selective binding of the agent. The fractionated sample can be, for example, a cell lysate or lipid membranes and the binding agent can be an antibody or a non-hydrolyzable substrate analog depending upon which inventive polypeptide is being assayed. For example, when the assay is directed to CAN-1 the fraction can be lipid membranes and the selective binding agent can be an antibody. Alternatively, when the assayed polypeptide is CAN-1, the fractionated sample can be a cell lysate and the binding agent can be an antibody or non-hydrolyzable substrate analog.

Essentially all modes of affinity binding assays are applicable for use in determining the amount of a polypeptide of the invention in a sample. Such methods are rapid, efficient and sensitive. Moreover, affinity binding methods are simple and can be adjusted to be performed in a variety of clinical settings and under conditions to suit a variety of particular needs. Affinity binding assays which are known and can be used in the methods of the invention include both soluble and solid phase formats. A specific, representative, example of a soluble phase affinity binding assay is immunoprecipitation using an antibody selective for CAN-1. Solid phase formats are advantageous for the methods of the invention since they are rapid and can be performed more easily on multiple different samples simultaneously without losing sensitivity or accuracy. Moreover, solid phase affinity binding assays are further amenable to high throughput screening and automation.

Specific examples of solid phase affinity binding assays include immunoaffinity binding assays such as an ELISA and radioimmune assay (RIA). Other solid phase affinity binding assays are known to those skilled in the art and are applicable to the methods of the invention. Although affinity binding assays are generally formatted for use with an antibody that is selective for the analyte or ligand of interest, essentially any binding agent can be alternatively substituted for selectively binding the antibody. Such binding agents include, for example, steroids, steroid derivatives, macromolecules such as polypeptides, peptides, nucleic acids, lipids and sugars as well as small molecule compounds. Methods are known in the art for identifying such molecules which bind selectively to a particular analyte or ligand and include, for example, combinatorial libraries. Thus, for a molecule other than an antibody to be used in an affinity binding assay, all that is necessary is for the binding agent to exhibit selective binding activity for the inventive polypeptide.

Various modes of affinity binding formats are similarly known which can be used in the diagnostic methods of the invention. For the purpose of illustration, particular embodiments of such affinity binding assays will be described further in reference to immunoaffinity binding assays. The various modes of affinity binding assays, such as immunoaffinity binding assays, include for example, solid phase ELISA and RIA as well as modifications thereof. Such modifications thereof include, for example, capture assays and sandwich assays as well as the use of either mode in combination with a competition assay format. The choice of which mode or format of immunoaffinity binding assay to use will depend on the intent of the user. Such methods can be found described in common laboratory manuals such as Harlow and Lane, *Using Antibodies: A Laboratory Manual*, Cold Spring Harbor Laboratory Press, New York (1999).

As with the hybridization methods described previously, the diagnostic formats employing affinity binding can be used in conjunction with a variety of detection labels and systems known in the art to quantitate amounts of a polypeptide of the invention in the analyzed sample. Detection systems include the detection of bound polypeptide of the invention by both direct and indirect means. Direct detection methods include labeling of an antibody or binding agent that binds specifically to a polypeptide of the invention. Indirect detection systems include, for example, the use of labeled secondary antibodies and binding agents.

Secondary antibodies, labels and detection systems are well known in the art and can be obtained commercially or by techniques well known in the art. The detectable labels and systems employed with a binding agent that is specific to a polypeptide of the invention should not impair binding of the agent to its cognate inventive polypeptide. Moreover, multiple antibody and label systems can be employed for detecting bound antigen/antibody complexes of the invention to enhance the sensitivity of the binding assay if desired.

As with the hybridization formats described previously, detectable labels can be essentially any label that can be quantitated or measured by analytical methods. Such labels include, for example, enzymes, radioisotopes, fluorochromes as well as chemi- and bioluminescent compounds. Specific examples of enzyme labels include horseradish peroxidase (HRP), alkaline phosphatase (AP), β-galactosidase, urease and luciferase.

A horseradish-peroxidase detection system can be used, for example, with the chromogenic substrate tetramethylbenzidine (TMB), which yields a soluble product in the presence of hydrogen peroxide that is detectable by measuring absorbance at 450 mm. An alkaline phosphatase detection system can be used with the chromogenic substrate p-nitrophenyl phosphate, for example, which yields a soluble product readily detectable by measuring absorbance at 405 nm. Similarly, a β-galactosidase detection system can be used with the chromogenic substrate o-nitrophenyl-β-D-galactopyranoside (ONPG), which yields a soluble product detectable by measuring absorbance at 410 nm, or a urease detection system can be used with a substrate such as urea-bromocresol purple (Sigma Immunochemicals, St. Louis, Mo.). Luciferin is the substrate compound for luciferase which emits light following ATP-dependent oxidation.

Fluorochrome detection labels are rendered detectable through the emission of light of ultraviolet or visible wavelength after excitation by light or another energy source. DAPI, fluorescein, Hoechst 33258, R-phycocyanin, B-phycoerythrin, R-phycoerythrin, rhodamine, Texas red and lissamine are specific examples of fluorochrome detection labels that can be utilized in the affinity binding formats of the invention. Particularly useful fluorochromes include fluorescein and rhodamine.

Chemiluminescent as well as bioluminescent detection labels are convenient for sensitive, non-radioactive detection of the inventive polynucleotides and polypeptides and can be obtained commercially from various sources such as Amersham Lifesciences, Inc. (Arlington Heights, Ill.).

Radioisotopes can alternatively be used as detectable labels for use in the binding assays of the invention. Iodine-125 is a specific example of a radioisotope useful for a detectable label.

Signals from detectable labels can be analyzed, for example, using a spectrophotometer to detect color from a chromogenic substrate; a fluorometer to detect fluorescence in the presence of light of a certain wavelength; or a radiation counter to detect radiation, such as a gamma counter for detection of iodine-125. For detection of an enzyme-linked secondary antibody, for example, a quantitative analysis of the amount of bound agent can be made using a spectrophotometer such as an EMAX Microplate Reader (Molecular Devices, Menlo Park, Calif.) in accordance with the manufacturer's instructions. If desired, the assays of the invention can be automated or performed robotically, and the signal from multiple samples can be detected simultaneously.

The diagnostic formats of the present invention can be forward, reverse or simultaneous as described in U.S. Pat. No. 4,376,110 and No. 4,778,751. Separation steps for the various assay formats described herein, including the removal of unbound secondary antibody, can be performed by methods known in the art (Harlow and Lane, supra). For example, washing with a suitable buffer can be followed by filtration, aspiration, vacuum or magnetic separation as well as by centrifugation.

In yet another aspect, the present invention provides methods for identifying a binding partner of a CAN-1, STG or SEEK-1 polypeptide, the methods comprising the steps of (a) contacting a CAN-1, STG or SEEK-1 polypeptide with a binding partner (such as a monoclonal or polyclonal antibody); and (b) determining whether the binding partner affects a biological activity of the polypeptide.

The methods of this aspect of the invention may include contacting a sample containing the CAN-1, STG or SEEK-1 polypeptide, and an appropriate substrate, with a test compound under conditions that allow product formation from the substrate, and measuring the amount of the product formation from the substrate. A decrease in the amount of product formation from the polypeptide substrate in the presence of the test compound compared to the absence of the test compound indicates that the compound has inhibitory activity towards the inventive polypeptide activity. Similarly, compounds that increase the activity of a CAN-1, STG or SEEK-1 polypeptide also can be identified. A test compound added to a sample containing a CAN-1, STG or SEEK-1 polypeptide and an appropriate substrate which increases the amount of product or rate of product formation or chemical modification of the substrate, compared to the absence of the test compound, indicates that the compound increases the activity of the polypeptide. Therefore, in one aspect, the invention provides a method of identifying compounds that modulate the activity of the polypeptides of the present invention. The polypeptide-containing sample used for such a method can be serum, skin tissue, a keratinocyte cell population or a recombinant cell population expressing the inventive polypeptide.

The methods for determining the activity of a CAN-1, SEEK-1 or STG polypeptide in a sample described above can also be adapted for screening test compounds to determine their ability to inhibit or increase the enzymatic and/or biological activity of an inventive polypeptide. In such cases, a test compound is added to a reaction system and the effect of the test compound on production of product is observed. Those compounds which inhibit the product formation or rate of product formation are considered as potential antagonists of the inventive polypeptides and further as potential therapeutic agents for treatment of psoriasis. Similarly, those compounds which increase the product or rate of product formation are considered as potential agonists of the inventive polypeptides and further as potential therapeutic agents for the treatment of psoriasis.

A reaction system for identifying a compound that inhibits or enhances the activity of the inventive polypeptides can be performed using essentially any source of inventive polypeptide activity. Such sources include, for example, a skin cell sample, lysate or fractionated portion thereof, a bodily fluid such as blood, serum or urine from an individual with psoriasis; a recombinant cell or soluble recombinant source, and an in vitro translated source. The source of inventive polypeptide is combined with an appropriate substrate as described above and incubated in the presence or absence of a test inhibitory compound. The reaction rate or extent of the usage of the substrate in the presence of the test compound is compared with that in the absence of the test compound. Those test compounds which provide inhibition of the reaction activity of at least about 50% are considered to be inhibitors of the inventive polypeptides. Similarly, those compounds which increase the reaction activity of two-fold or more are considered to be enhancers of the activity of the inventive polypeptides. Such inhibitors of the inventive polypeptides can then be subjected to further in vitro or in vivo testing to confirm that they inhibit the production of substrates of the inventive polypeptides in cellular and animal models.

Suitable test compounds for the inhibition or enhancement assays can be any substance, molecule, compound, mixture of molecules or compounds, or any other composition which is suspected of being capable of inhibiting inventive polypeptide activity in vivo or in vitro. The test compounds can be heterocyclic organic compounds such as steroids or steroid derivatives, macromolecules, such as biological polymers, including polypeptides, polysaccharides and nucleic acids. Sources of test compounds which can be screened for inhibitory activity against the inventive polypeptides include, for example, libraries of peptides, polypeptides, DNA, RNA and small organic compounds. Additionally, test compounds can be preselected based on a variety of criteria. For example, suitable test compounds for CAN-1 can be selected, for example, randomly and tested by the screening methods of the present invention. Test compounds are administered to the reaction system at a concentration in the range from about 1 nM to 1 mM. Useful test compounds such as steroids and steroid derivatives are lipophilic, thus allowing them to cross the cell membrane. In addition, routine ligand specific targeting methods are useful for testing compounds for inhibitory activity.

Therefore, in one aspect, the invention provides methods of identifying a compound that inhibits or enhances the activity of a CAN-1, SEEK-1 or STG polypeptide where the sample further consists of a skin cell lysate, a recombinant cell lysate expressing a CAN-1, SEEK-1 and/or STG polypeptide, an in vitro translation lysate containing mRNA encoding CAN-1, SEEK-1 or STG polypeptide, a fractionated sample of a skin cell lysate, a fractionated sample of a recombinant cell lysate expressing CAN-1, SEEK-1 or STG polypeptide, a fractionated sample of an in vitro translation lysate containing mRNA encoding a CAN-1, SEEK-1 or STG polypeptide or an isolated CAN-1, SEEK-1 or STG polypeptide. The method can be in single or multiple sample format.

In another aspect, the present invention provides methods for ameliorating the symptoms and/or progression of psoriasis, the methods comprising administering to an individual suffering from psoriasis an inhibitory amount of a selective inhibitor of at least one polypeptide chosen from the group consisting of CAN-1, STG and SEEK-1, wherein the inhibitory amount causes a reduction (such as, by way of non-limiting example, a reduction of about 2-fold) in the amount and/or activity of the chosen polypeptide(s). A representative example of a selective inhibitor is an antisense polynucleotide that is complementary to all, or to a portion, of a nucleic acid molecule (such as an mRNA molecule) that encodes a CAN-1, STG or SEEK-1 polypeptide.

Such inhibitors may be produced using methods which are generally known in the art, and include the use of purified CAN-1, SEEK-1 or STG polypeptide to produce antibodies or to screen libraries of compounds, as described previously, for those which specifically bind to CAN-1, SEEK-1 or STG polypeptide. Lipophilic compounds able to cross the lipid bilayer that makes up cell membranes are especially useful inhibitors for practicing the methods of the invention.

Antibodies specific to CAN-1 can be used, for example, directly as an antagonist. The antibodies can be generated using methods that are well known in the art and include, for example, polyclonal, monoclonal, chimeric, humanized single chain, Fab fragments, and fragments produced by a Fab expression library.

It is preferred that antibodies of the present invention are CDR-grafted antibodies. The term "CDR-grafted antibody" as used herein refers to an antibody molecule wherein the heavy and/or light chain contains one or more CDRs from a donor antibody (e.g., a murine monoclonal antibody) grafted into a heavy and/or light chain variable region framework of an acceptor antibody (e.g., human antibody). Construction of CDR-grafted antibodies is fully described in European Patent Application EP-A-0239400, which publication is incorporated herein by reference.

The earliest work on humanising monoclonal antibodies by CDR-grafting was carried out on monoclonal antibodies recognizing synthetic antigens, such as NP or NIP antigens. However, examples in which a mouse monoclonal antibody recognizing lysozyme and a rat monoclonal antibody recognizing an antigen on human T-cells were humanised by CDR-grafting have been described by Verhoeyen et al (*Science,* 239: 1534-1536 (1988)), and Riechmann et al (*Nature,* 332: 323-324 (1988)), respectively.

In Riechmann et al, it was found that the transfer of the CDR regions alone (as defined by Kabat et al, 1987, in Sequences of Proteins of Immunological Interest, US Department of Health and Human Services, NIH, USA; and Wu et al, *J. Exp. Med.,* 132: 211-250 (1970)) was not sufficient to provide satisfactory antigen binding activity in the CDR-grafted product. It was found that a number of framework residues have to be altered so that they correspond to those of the donor framework region. Proposed criteria for selecting which framework residues need to be altered are described in International Patent Application WO 90/07861, which publication is incorporated herein by reference.

In another embodiment of the invention, the nucleic acid molecules encoding a CAN-1, SEEK-1 or STG polypeptide, or any fragment thereof, or antisense molecules complementary to all or part of a nucleic acid molecule encoding a CAN-1, SEEK-1 or STG polypeptide, are used for therapeutic purposes. In one aspect, antisense molecules complementary to nucleic acid molecules encoding a CAN-1, SEEK-1 or STG polypeptide are used to block the transcription or translation of an mRNA homologous to the antisense molecule. Specifically, cells are transformed with sequences complementary to mRNA transcripts encoding a CAN-1, SEEK-1 or STG polypeptide. Such methods are well known in the art, and sense or antisense oligonucleotides or larger polynucleotide fragments, can be designed from various locations along the coding or control regions of sequences encoding the inventive polypeptides. Thus, antisense molecules may be used to modulate the activity of the inventive polypeptides, or to achieve regulation of gene function.

Expression vectors derived from retroviruses, adenovirus, adeno-associated virus (AAV), herpes or vaccinia viruses, or from various bacterial plasmids can be used for delivery of antisense nucleotide sequences to a skin cell population. The viral vector selected should be able to infect the skin cells and be safe to the host and cause minimal cell transformation. Retroviral vectors and adenoviruses offer an efficient, useful, and well characterized means of introducing and expressing foreign genes efficiently in mammalian cells. These vectors are well known in the art and have very broad host and cell type ranges, express genes stably and efficiently. Methods which are well known to those skilled in the art can be used to construct such recombinant vectors and are described in Sambrook et al. (supra). Even in the absence of integration into the DNA, such vectors can continue to transcribe RNA molecules for a substantial period of time. Transient expression can last for a month or more with a non-replicating vector and even longer if appropriate replication elements are part of the vector system.

Ribozymes, enzymatic RNA molecules, can also be used to catalyze the specific cleavage of mRNAs encoding CAN-1, SEEK-1 or STG. The mechanism of ribozyme action involves sequence-specific hybridization of the ribozyme molecule to a complementary target RNA, followed by endonucleolytic cleavage. Specific ribozyme cleavage sites within any potential RNA target are identified by scanning a target RNA for ribozyme cleavage sites which include, for example, the following sequences: GUA, GUU, and GUC. Once identified, short RNA sequences of between 10 and 20 ribonucleotides corresponding to the region of the target polynucleotide containing the cleavage site can be evaluated for secondary structural features which can render the oligonucleotide inoperable. The suitability of candidate targets can also be evaluated by testing accessibility to hybridization with complementary oligonucleotides using ribonuclease protection assays. Antisense molecules and ribozymes of the invention can be prepared by any method known in the art for the synthesis of nucleic acid molecules.

In another embodiment, the CAN-1, SEEK-1 or STG promoter and regulatory regions can be used for constructing vectors for psoriasis therapy. The promoter and regulatory region can be operatively fused to a therapeutic polynucleotide for keratinocyte-specific expression. This method can include the addition of one or more enhancer elements which amplify expression of the heterologous therapeutic polynucleotide without compromising tissue specificity.

It is understood that modifications which do not substantially affect the activity of the various embodiments of this invention are also included within the definition of the invention provided herein. Accordingly, the following examples are intended to illustrate but not limit the present invention.

EXAMPLE 1

Identification and Characterization of CAN-1

As part of a detailed sequence analysis of the publicly deposited DNA sequence surrounding the HLA C locus on human chromosome 6, a novel candidate coding sequence (a.k.a. CAN-1) was identified based upon its chromosomal position relative to the psoriasis associated HLA Cw6 allele, and its relatively strong RNA expression level in skin. The CAN-1 transcript unit is located on chromosome 6 approximately 132 kilobases (kb) telomeric away from the HLA Cw6 allele.

A genomic DNA sequence was obtained from the publicly available databases (e.g. GenBank) for a cosmid clone (AC004195), which is located 130 kb telomeric from HLA-C. Based on a literature report of a gene (pg8) in this region being expressed in skin (Guillaudeux et al. *PNAS* 95:9494-9499, 1998) the entire cosmid sequence was screened for potential exons using Genscan (Burge, C. and Karlin, S., Prediction of complete gene structures in human genomic DNA. *J. Mol. Biol.* 268, 78-94, 1997). The Genscan program predicted the existence of three exons in the AC004195 cosmid clone insert DNA that were not previously described. One of the exons showed DNA sequence homology to six mouse IMAGE EST cDNA clones that were all derived from skin. The sequence information from the mouse EST clones was assembled into one reference sequence and then compared to the human genomic sequence from AC004195. This led to the identification of two exons in the human sequence, exon one, identified by Genscan, and exon two only partially identified by Genscan. Using both the mouse EST sequence and human genomic exons as a guide, additional searching of Genbank dbest database revealed one partially overlapping human fetal heart cDNA and two additional mouse skin ESTs that appeared to be similar.

To find out if these two exons identified above were expressed in human tissues, PCR primers were designed for these exons and tested for the ability to detect these exons in a number of human tissue sources. The predicted exons were detected only in cDNA prepared from human skin.

The two exon transcription unit was designated as CAN-1. Using 5' RACE to extend the 5' untranslated region sequence, a cDNA sequence was determined and found to have 891 nucleotides (SEQ ID NO:1). A polyadenylation signal site (AATAAA) is located 18 base pairs (bp) from a poly-A tail. The largest open reading frame identified in the CAN-1 cDNA sequence (SEQ ID NO:1) is 408 bp (or 136 amino acids (SEQ ID NO:2)). Analysis of the predicted polypeptide (SEQ ID NO:2) revealed the presence of a predicted signal peptide (amino acids 1 to 22 of SEQ ID NO:2) and cleavage site (amino acid 22 of SEQ ID NO:2). This suggests that the entire coding sequence for CAN-1 has been identified. The amino acid sequence of the mature CAN-1 polypeptide (without the signal peptide) is set forth in SEQ ID NO:3. Comparison of the human and mouse amino acid sequences shows that they are 73% conserved. However, a BLAST computer search of the public databases did not reveal any significant polypeptide homologies between the CAN-1 polypeptide (SEQ ID NO:2) and any known or predicted polypeptides in Genbank.

EXAMPLE 2

Expression Profile of CAN-1 in Human Tissues

To test what tissues expressed human CAN-1, PCR was used to examine cDNA prepared from mRNA transcripts isolated from thirty-two different human tissues. All tissues were purchased from commercial sources (Invitrogen, Carlsbad, Calif., Clontech, Palo Alto, Calif. Biochain Hayward, Calif.), except for PBL (peripheral blood lymphocytes) and bone which were prepared in-house. The tissue sources assayed were: heart, small intestine, mammary gland, spleen, prostate, stomach, skeletal muscle, thymus, skin, uterus, kidney bone marrow, liver, colon, lung, trachea, pancreas, brain, salivary gland, cerebellum, thyroid, fetal brain, parotid, fetal liver, umbilical cord, spinal cord, ovary, placenta, PBL, adrenal gland, and bone.

cDNA was prepared from 5 µg of total RNA using an oligo dT primer and standard reverse transcription methods according to manufacturers' protocols. (Gibco BRL Cat No. 18089-011, Frohman, 1985).

15 ng/µl aliquots of each cDNA sample were subjected to PCR amplification using primers [DMO 9299: GACTCAGC-CCACCCCAGCTTT (SEQ ID NO:11)] and [DMO 8932: CCGGGGTGGGTCTAGGTCT (SEQ ID NO:12)]. PCR cycling conditions were 94° C. 30 s, 62° C. 30 s, 72° C. 30 sec for 35 cycles. The resulting amplified DNA products were separated using gel electrophoresis and according to this analysis, CAN-1 is readily detected in only the normal skin cDNA sample, and the only other tissue showing slight expression was thymus.

EXAMPLE 3

CAN-1 Sequence Polymorphisms

CAN-1 polynucleotide sequences from 12 different humans subjects were analyzed for DNA polymorphisms that might affect the function of the encoded polypeptide. Twelve psoriatic human subjects were analyzed, and three non-psoriatic controls. Numerous single nucleotide polymorphisms (SNPs) were found in and around the coding sequence for the CAN-1 polypeptide. The location and identity of the polymorphisms are set forth in Table 1. The locations of the polymorphisms are with reference to the numbering of the CAN-1 genomic nucleotide sequence set forth in SEQ ID NO:4.

TABLE 1

| CAN-1 single nucleotide polymorphism | Location |
|---|---|
| T | 118 |
| A | 365 |
| A | 554 |
| G | 970 |
| T | 1100 |
| A | 1200 |
| T | 1394 |
| A | 1681 |
| T | 1879 |
| A | 1986 |
| C | 2020 |
| G | 2111 |
| T | 2397 |
| G | 2655 |
| G | 2822 |
| C | 2875 |

One SNP is a T at position 311 of the CAN-1 cDNA sequence set forth in SEQ ID NO:1.

Additionally, a CAN-1 gene polymorphism was observed in which the nucleic acid sequence CAAG was deleted at positions twelve through fifteen of the CAN-1 genomic nucleotide sequence set forth in SEQ ID NO:4. The nucleic acid sequence of this deletion polymorphism is set forth in SEQ ID NO:10. Thus, in one aspect, the present invention provides isolated genomic DNA molecules that encode a CAN-1 polypeptide, and that are at least 70% identical (such as at least 80% identical, at least 90% identical, at least 95% identical or at least 99% identical) to the genomic DNA molecule set forth in SEQ ID NO:10. The exons in the CAN-1 gene consisting of the sequence set forth in SEQ ID NO:10 are located at the following positions: nucleic acid residue 1481 through nucleic acid residue 1535, and nucleic acid residue 2202 through nucleic acid residue 2557.

One or more of the SNPs described in and around the CAN-1 gene are likely useful for predicting either the onset of psoriasis, or the likely outcome following a particular therapeutic treatment.

EXAMPLE 4

Identification and Characterization of STG

Using a large continuous sequence of DNA deposited and available in the public databases, the Genscan computer program predicted the existence of a gene called U8, and later called STG by Oka et al. Human Mol. Genet. 8(12):2165-2170 (1999).

The specificity of the expression of the human STG coding sequence was examined by PCR analysis of cDNA samples prepared from mRNA transcripts isolated from thirty-six (36) different human tissues. The tissue sources assayed were: heart, small intestine, mammary gland, spleen, prostate, stomach, skeletal muscle, thymus, skin, uterus, kidney, bone marrow, liver, colon, lung, trachea, pancreas, brain, salivary gland, cerebellum, thyroid, fetal brain, parotid, fetal liver, umbilical cord, spinal cord, ovary, placenta, PBL, adrenal gland, testis, adipose tissue, cartilage, fetal skin, stimulated PBL and bone.

Aliquots of each cDNA tissue sample were subjected to 35 cycles of PCR amplification using primers TCCTCTGGGC-CTGCTCCT [DMO14104] (SEQ ID NO:13) and GTC-CGAGCTGAGGCAAGTTG [DMO14030] (SEQ ID NO:14) and the resulting amplified DNA products separated using gel electrophoresis. According to this analysis, STG transcription products were detected in 5 out of the 36 tissues tested, including skin and fetal skin (data not shown). The level of expression observed in the skin samples was as high as for any of the other tissues. Further, in a panel of skin samples from eleven individuals, it appears that multiple individuals expressed STG in their skin. Also, and possibly most importantly, the STG encoding transcript was found to be expressed highly in a kerafinocyte sample.

Based on the physical location of the STG coding sequence (near the HLA-C locus on human chromosome 6), the STG polypeptide is a candidate to be involved in the genetic susceptibility towards psoriasis. Furthermore, the fact that the STG coding sequence is expressed in skin samples, and particularly in keratinocytes, suggests that the STG polypeptide may have a function important at the site of the psoriatic lesion. For these reasons in particular, STG appears to be a target for intervention in the psoriasis disease process.

EXAMPLE 5

STG Sequence Polymorphisms

STG polynucleotide sequences from nine psoriatic humans subjects were analyzed for DNA polymorphisms that might affect the function of the STG polypeptide. Numerous SNPs were found in and around the STG coding sequence (see Table 2). Some of these polymorphisms affect amino acids in the polypeptide product, and thus may be of functional relevance. Other of the polymorphisms are located in 5' or 3' untranslated regions of the STG gene, and may have some functional importance in the regulation of the expression of the STG polypeptide.

TABLE 2

SNPs discovered by sequencing in and around the STG gene. The location of the SNPs is with reference to the STG genomic DNA sequence set forth in SEQ ID NO: 7.

| STG single nucleotide polymorphism | Location |
|---|---|
| G | 17 |
| G | 32 |
| C | 45 |
| G | 116 |
| A | 171 |
| G | 178 |
| C | 198 |
| C | 238 |
| C | 356 |
| C | 364 |
| G | 379 |
| C | 393 |
| C | 511 |

TABLE 2-continued

SNPs discovered by sequencing in and around the STG gene. The location of the SNPs is with reference to the STG genomic DNA sequence set forth in SEQ ID NO: 7.

| STG single nucleotide polymorphism | Location |
| --- | --- |
| G | 626 |
| C | 665 |
| C | 730 |
| C | 3365 |
| A | 3451 |
| G | 3483 |
| A | 3497 |
| C | 4969 |

The SNPs that occur within the open reading frame encoding the STG protein product are shown in Table 3 wherein the location of the SNPs is with reference to the STG cDNA sequence set forth in SEQ ID NO:5.

TABLE 3

| STG single nucleotide polymorphism (amino acid substitution shown) | Location |
| --- | --- |
| A (Arg) | 142 |
| C (Ala) | 242 |
| C (Pro) | 247 |
| T (silent) | 492 |
| A (Lys) | 493 |
| C (silent) | 900 |

EXAMPLE 6

Identification and Characterization of SEEK-1

A cDNA was submitted to Genbank (Accession No. AB031479) which was reported to be near the HLA C gene. There were no significant polypeptide homologies detected by using the SEEK-1 deduced polypeptide sequence to search the public database using the BLAST program.

The specificity of the expression of the human SEEK-1 coding sequence was examined by PCR analysis of cDNA samples prepared from mRNA transcripts isolated from thirty-six (36) different human tissues. The tissue sources assayed were: heart, small intestine, mammary gland, spleen, prostate, stomach, skeletal muscle, thymus, skin, uterus, kidney bone marrow, liver, colon, lung, trachea, pancreas, brain, salivary gland, cerebellum, thyroid, fetal brain, parotid, fetal liver, umbilical cord, spinal cord, ovary, placenta, PBL, adrenal gland, testis, adipose tissue, cartilage, fetal skin, stimulated PBL and bone. Expression of the SEEK-1 transcript was also examined using a psoriatic tissue panel composed of 11 patient samples from psoriatic skin lesions and uninvolved skin.

Aliquots of each cDNA tissue sample were subjected to 35 cycles of PCR amplification using primers GGAACCAG-GATATCCTCCTGTGT [DMO14027] (SEQ ID NO:15) and ACCCCAGCTCCTTAACACAGATC [DMO14102] (SEQ ID NO:16) and the resulting amplified DNA products separated using gel electrophoresis. According to this analysis, SEEK-1 cDNA was readily detected in 8 out of the 36 tissues tested, including skin and fetal skin (data not shown). More specifically, SEEK-1 expression products were only detected in a subset of the tissues tested, including skin, fetal skin, testis, uterus, prostate, mammary gland, ovary and colon (data not shown). In a panel of skin samples, it appears that multiple individuals express SEEK-1 in their skin. Also, the SEEK-1 coding sequence was found to be expressed highly in a keratinocyte sample.

EXAMPLE 7

Bacterial Expression of CAN-1, STG and SEEK-1

This example sets forth a representative protocol for expressing CAN-1, STG or SEEK-1 protein. A nucleic acid molecule encoding a polypeptide of the present invention is amplified using PCR oligonucleotide primers corresponding to the 5' and 3' ends of DNA sequences encoding CAN-1, STG or SEEK-1 to synthesize polynucleotide fragments that encode CAN-1, STG or SEEK-1 polypeptide. The primers used to amplify the cDNA insert should preferably contain restriction sites, such as BamHI and XbaI, at the 5' end of the primers in order to clone the amplified product into the expression vector. For example, NdeI and XhoI correspond to the restriction enzyme sites on the bacterial expression vector pET-23a. (Novagen, Inc, Madison, Wis.). This plasmid vector encodes antibiotic resistance (Amp$^r$), a bacterial origin of replication (ori), an IPTG-regulatable promoter/operator (P/O), a ribosome binding site (RBS), a 6-histidine tag (6-His), and restriction enzyme cloning sites.

The pET-23a vector is digested with NdeI and XhoI and the amplified fragment is ligated into the pET-23a vector maintaining the reading frame initiated at the bacterial RBS. The ligation mixture is then used to transform the *E. coli* strain BL21(DE3)pLysS (Novagen, Inc). Transformants are identified by their ability to grow on LB plates and ampicillin-resistant colonies are selected. Plasmid DNA is isolated and confirmed by restriction analysis.

Clones containing the desired constructs are grown overnight (O/N) in liquid culture in LB media supplemented with Ampicillin (100 µg/ml). The O/N culture is used to inoculate a large culture at a ratio of 1:20 to 1:50. The cells are grown to an optical density 600 nm (O.D.$_{600}$) of between 0.6 and 1.5. IPTG (Isopropyl-B-D-thiogalacto pyranoside) is then added to a final concentration of 0.5 mM.

Cells are grown for an extra 2 to 4 hours at 30 to 37° C. Cells are then harvested by centrifugation (10 mins at 6000× g). The cells are then lysed by sonication using three 30 second pulses on a Sonifer 450 (Branson Ultrasonics Corp., Danbury, Conn.). The cell debris is removed by centrifugation, and the supernatant containing the polypeptide is loaded onto a nickel-nitrilo-tri-acetic acid ("Ni-NTA") affinity resin column (available from Qiagen, Inc., Chatsworth, Calif.). Polypeptides with a 6×His tag bind to the Ni-NTA resin with high affinity and can be purified in a simple one-step procedure (for details see: The QIAexpressionist, Fourth Edition (2000) QIAGEN, Inc., supra).

Briefly, the supernatant is loaded onto the column in 10 mM imidazole, the column is washed with 20 volumes of 20 mM imidazole, and the soluble polypeptide is eluted with 250 mM imidazole. Imidazole is removed by a final dialyzing step against PBS or 50 mM sodium acetate pH 6 buffer plus 200 mM NaCl. The purified polypeptide is stored at 4° C. or frozen at −80° C.

EXAMPLE 8

Purification of CAN-1, STG and SEEK-1 from an Inclusion Body

The following method can also be used to purify a CAN-1, STG or SEEK-1 polypeptide expressed in *E. coli* when the polypeptide is present in the form of inclusion bodies. Unless otherwise specified, all of the following steps are conducted at 4-10° C.

Upon completion of the production phase of the *E. coli* fermentation, the cell culture is cooled to 4-10° C. and the cells harvested by continuous centrifugation at 15,000 rpm (Heraeus Sepatech). On the basis of the expected yield of polypeptide per unit weight of cell paste and the amount of purified polypeptide required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer Microfluidics, Corp. or APV Gaulin, Inc.) twice at 4000-6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2-4 hours. After 7000×g centrifugation for 15 min., the pellet is discarded and the polypeptide containing supernatant is incubated at 4° C. overnight to allow further GuHCl extraction.

Following high speed centrifugation (30,000×g) to remove insoluble particles, the GuHCl solubilized polypeptide is refolded by quickly mixing the GuHCl extract with 20 volumes of buffer containing 50 mM sodium, pH 4.5, 150 mM NaCl, 2 mM EDTA by vigorous stirring. The refolded diluted polypeptide solution is kept at 4° C. without mixing for 12 hours prior to further purification steps.

To clarify the refolded polypeptide solution, a previously prepared tangential filtration unit equipped with 0.16 µm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Coomassie blue stained 16% SDS-PAGE gel when 5 µg of purified polypeptide is loaded.

EXAMPLE 9

Cloning and Expression of CAN-1, STG and SEEK-1 in a Baculovirus Expression System In this example the plasmid shuttle vector pFastBac1 (Life Technologies Inc., Rockville, Md.) is used to insert a polynucleotide into a baculovirus to express an inventive polypeptide. This expression vector contains the strong polyhedrin promoter of the *Autographa californica* nuclear polyhedrosis virus (AcMNPV) followed by convenient restriction sites such as BamHI, XbaI and EcoRI. The polyadenylation site of the simian virus 40 ("SV40") is used for efficient polyadenylation. The gene of interest is cloned into the pFastBac1 donor plasmid, and the recombinant plasmid is transformed into DH10Bac (Life Technologies, Inc.) competent cells which contain the bacmid with a mini-attTn7 target site and the helper plasmid. The mini-Tn7 element on the FastBac donor plasmid can transpose to the mini-attTn7 target site on the bacmid in the presence of transposition polypeptides provided by the helper plasmid. Colonies containing recombinant bacmids are identified by the disruption of the lacZalpha gene on the bacmid. High molecular weight mini-prep DNA is prepared from selected *E. coli* clones containing the recombinant bacmid, and this DNA is used to transfect insect cells.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31, 1989.

Specifically, the cDNA sequence of a clone encoding a CAN-1, STG or SEEK-1 polypeptide, including the AUG initiation codon and the naturally associated leader sequence, is amplified using the PCR. If the naturally occurring signal sequence is used to produce a secreted polypeptide (as could be done with the CAN-1 polypeptide), the pFastBac1 vector does not need a second signal peptide. Alternatively, the vector can be modified to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified PCR fragment is cloned into a TA cloning vector (such as "The Original TA Cloning Kit" Invitrogen Inc., Carlsbad, Calif.). The resulting plasmid is then digested with the appropriate restriction enzymes and the correct fragment is excised and purified from a 1% agarose gel using a commercially available kit ("Qiaquick Gel Extraction Kit" Qiagen Inc., Valencia, Calif.).

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Qiaquick Gel Extraction Kit" Qiagen Inc., Valencia, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

After the recombinant pFastBac donor plasmid has been determined to be correct, the DNA is transformed into DH10Bac for transposition into the bacmid. White colonies contain the recombinant bacmid are selected for isolation of recombinant bacmid DNA. Sf9 insect cells (ATCC CRL 1711) are then transfected with the recombinant bacmid DNA. Recombinant baculovirus are harvested from the cell culture media at 72 hours post-transfection. The baculovirus particles are then used for infection into Sf9 cells at a starting multiplicity of infection (MOI) of 5 to 10. The cells are incubated for 24 to 96 hours and harvested by centrifugation. The polypeptides in the supernatant as well as the intracellular polypeptides are analyzed by SDS-PAGE. Microsequencing of the amino acid sequence of the amino terminus of purified polypeptide may be used to determine the amino terminal sequence of the produced polypeptide.

EXAMPLE 10

Expression of CAN-1, STG and SEEK-1 in Mammalian Cells

The polypeptides of the present invention can be expressed and secreted from a mammalian cell. A typical mammalian expression vector contains a promoter element, which mediates the initiation of transcription of mRNA, a polypeptide coding sequence, and signals required for the termination of transcription and polyadenylation of the transcript. Additional elements can include enhancers, Kozak polypeptide synthesis initiation sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter). Expression vectors may also contain epitope tags or polypeptide fusions such as FLAG (Sigma-Aldrich Inc., St. Louis, Mo.) or 6×His to aid in purification and detection of the recombinant polypeptide.

Suitable expression vectors for use in practicing the present invention include, for example, vectors such as pSVL and pMSG (Pharmacia, Uppsala, Sweden), pcDNA3.1 (Invitrogen Inc.), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The polynucleotide is cloned into an expression vector with a selectable marker such as dhfr, gpt, neomycin, hygromycin allowing the selection, identification and isolation of the transfected cells.

The transfected polynucleotide can also be amplified to express large amounts of the encoded polypeptide. The DHFR (dihydrofolate reductase) marker is useful in developing cell lines that carry several hundred or even several thousand copies of the polynucleotide of interest. (See, e.g., Alt, et al., *J. Biol. Chem.* 253:1357, 1978; Hamlin et al., *Biochem. et Biophys. Acta,* 1097:107, 1990; Page et al., *Biotechnology* 9:64, 1991). Another useful selection marker is the enzyme glutamine synthase (GS) (Murphy et al., *Biochem J.* 227:277, 1991; Bebbington et al., *Bio/Technology* 10: 169, 1992). Using these markers, the mammalian cells are grown in selective medium and the cells with the highest resistance are selected. These cell lines contain the amplified polynucleotides integrated into a chromosome. Chinese hamster ovary (CHO) and NSO cells are often used for the production of polypeptides.

Derivatives of the plasmid pSV2-dhfr (ATCC Accession No. 37146), the expression vectors pC4 (ATCC Accession No. 209646) and pC6 (ATCC Accession No. 209647) contain the strong promoter (LTR) of the Rous Sarcoma Virus (Cullen et al., *Molecular and Cellular Biology,* 438-447, March, 1985) plus a fragment of the CMV-enhancer (Boshart et al., *Cell* 41:521-530, 1985). Multiple cloning sites, e.g., with the restriction enzyme cleavage sites BamHI, XbaI and Asp718, facilitate the cloning of the polynucleotide of interest. The vectors also contain the 3' intron, the polyadenylation termination signal of the rat preproinsulin gene, and the mouse DHFR gene under control of the SV40 early promoter.

Specifically, the plasmid pC6, for example, is digested with appropriate restriction enzymes and then dephosphorylated using calf intestinal phosphatase by procedures known in the art. The vector is then isolated from a 1% agarose gel.

If the naturally occurring signal sequence is used to produce the secreted polypeptide, the vector does not need to supply a signal peptide. (such as pC6 or pcDNA3.1) Alternatively, if the naturally occurring signal sequence is not used, a vector can be used which contains a heterologous signal peptide, such as the mouse Igkappa-chain leader sequence used in the vector pSecTag2 A (Invitrogen Inc.)

The amplified PCR fragment is cloned into a TA cloning vector (such as "The Original TA Cloning Kit" Invitrogen Inc., Carlsbad, Calif.). The resulting plasmid is then digested with the appropriate restriction enzymes and the correct fragment is excised and purified from a 1% agarose gel using a commercially available kit ("Qiaquick Gel Extraction Kit" Qiagen Inc., Valencia, Calif.).

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Qiaquick Gel Extraction Kit" Qiagen Inc., Valencia, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

The resulting expression vector can then be transiently transfected into a suitable mammalian host, such as Cos-1, HEK 293 or CHO-K1 using electroportation, lipofectin or DEAE-Dextran (Sigma-Aldrich Inc., St. Louis Mo.) transfection methodologies. Expressed polypeptides are then harvested from the supernatent media after incubating 3-5 days. Alternatively, stable transfected cells can be isolated following 10-14 days of incubation with the appropriate antibiotic, such as 1 mg/ml G418.

When pursuing polynucleotide amplification following transfection, Chinese hamster ovary cells lacking an active DHFR gene can be used for transfection. Five µg of the expression plasmid pC6 is cotransfected with 0.5 μg of the plasmid pSVneo using lipofectin. The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate. The same procedure is repeated until clones are obtained which grow at a concentration of 100-200 μM. Expression of the desired product is analyzed, for instance, by SDS-PAGE and Western blot or by reversed phase HPLC analysis.

The polypeptide can be purified from the supernatent by loading onto an appropriate affinity resin column. Polypeptides with a 6×His tag bind to the Ni-NTA resin (available from Qiagen, Inc., Chatsworth, Calif.) with high affinity and can be purified in a simple one-step procedure. Alternatively, polypeptides with a FLAG epitope can be one-step purified using an anti-FLAG M2 monoclonal antibody agarose affinity gel (Sigma-Aldrich Inc.).

EXAMPLE 11

Polypeptide Fusions of CAN-1, STG and SEEK-1

The polypeptides of the present invention can be fused to other polypeptides. These fusion polypeptides can be used for a variety of applications. For example, fusion of the present polypeptides to His-tag, HA-tag, protein A, IgG domains, and maltose binding protein facilitates purification. (See EP A 394,827; Traunecker, et al., *Nature* 331:84, 1988). Similarly, fusion to IgG-1, IgG-3, and albumin increases the half life time in vivo. Nuclear localization signals fused to the polypeptides of the present invention can target the polypeptide to a specific subcellular localization, while covalent heterodimer or homodimers can increase or decrease the activity of a fusion polypeptide. Fusion polypeptides can also create chimeric molecules having more than one function. Finally, fusion polypeptides can increase solubility and/or stability of the fused polypeptide compared to the non-fused polypeptide. All of the types of fusion polypeptides described above can be made by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 1, is ligated into this BamHI site. Note that the polynucleotide is cloned without a stop codon, otherwise a fusion polypeptide will not be produced.

If the naturally occurring signal sequence is used to produce the secreted polypeptide, pC4 does not need a second signal peptide. Alternatively, if the naturally occurring signal sequence is not used, the vector can be modified to include a heterologous signal sequence. (See, e.g., WO 96/34891.)

EXAMPLE 12

Production of Antibodies Specific to CAN-1, STG and SEEK-1

The antibodies of the present invention can be prepared by a variety of methods. For example, cells expressing a polypeptide of the present invention is administered to an animal to induce the production of sera containing polyclonal antibodies. In a preferred method, a preparation of the secreted polypeptide is prepared and purified to render it substantially free of natural contaminants. Such a preparation is then introduced into an animal in order to produce polyclonal antisera of greater specific activity.

In the most preferred method, the antibodies of the present invention are monoclonal antibodies (or polypeptide binding fragments thereof). Such monoclonal antibodies can be prepared using hybridoma technology. (Köhler et al., *Nature* 256:495, 1975; Köhler et al., *Eur. J. Immunol.* 6:511, 1976; Köhler et al., *Eur. J. Immunol.* 6:292, 1976; Hammerling et al., in: Monoclonal Antibodies and T-Cell Hybridomas, Elsevier, N.Y., pp. 563-681 (1981)). In general, such procedures involve immunizing an animal (preferably a mouse) with polypeptide or, more preferably, with a secreted polypeptide-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al. (*Gastroenterology* 80:225, 1981). The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, polypeptide specific antibodies are used to immunize an animal, preferably a mouse. The splenocytes of such an animal are then used to produce hybridoma cells, and the hybridoma cells are screened to identify clones which produce an antibody whose ability to bind to the polypeptide-specific antibody can be blocked by the polypeptide. Such antibodies comprise anti-idiotypic antibodies to the polypeptide-specific antibody and can be used to immunize an animal to induce formation of further polypeptide-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted polypeptide-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, *Science* 229:1202, 1985; Oi et al., *BioTechniques* 4:214, 1986; Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643, 1984; Neuberger et al., *Nature* 314:268, 1985).

In some embodiments, for in vivo use of antibodies in humans, the antibody can be modified by attachment of polyethylene glycol (PEG) to extend the lifetime of the antibody.

EXAMPLE 13

Method of Detecting Abnormal Levels of a Polypeptide in a Biological Sample

A CAN-1, STG or SEEK-1 polypeptide can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at final concentration of 0.2 to 10 µg/ml. The antibodies can be monoclonal or polyclonal and are produced, for example, by the methods described supra. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 µl of specific antibody-alkaline phosphatase conjugate, at a concentration of 25-400 ng, is added and incubated for 2 hours at room temperature. The plates are again washed three times with deionized or distilled water to remove unbounded conjugate.

Add 75 µl of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance on the Y-axis (linear scale). Interpolate the concentration of the polypeptide in the sample using the standard curve.

EXAMPLE 14

Formulating a Polypeptide

Polypeptide compositions of the invention are formulated and dosed in a fashion consistent with good medical practice, taking into account the clinical condition of the individual patient (especially the side effects of treatment with the secreted polypeptide alone), the site of delivery, the method of administration, the scheduling of administration, and other factors known to practitioners. The "effective amount" for purposes herein is thus determined by such considerations.

As a general proposition, the total pharmaceutically effective amount of polypeptide administered parenterally per dose will be in the range of about 1 Tg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the polypeptide is typically administered at a dose rate of about 1 µg/kg/hour to about 50 µg/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the polypeptides of the invention are administered orally, rectally, parenterally, intracistenally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The polypeptides of the invention are also suitably administered by sustained-release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman, et al., *Biopolymers* 22:547, 1983), poly (2-hydroxyethyl methacrylate) (Langer et al., *J. Biomed. Mater. Res.* 15:167, 1981; Langer, *Chem. Tech.* 12:98, 1982), ethylene vinyl acetate (Langer et al.) or poly-D-(−)-3-hydroxybutyric acid (EP 133, 988). Sustained-release compositions also include liposomally entrapped polypeptides. Liposomes containing the polypeptides are prepared by methods known per se: e.g., DE 3,218,121; Epstein et al., *Proc. Natl. Acad. Sci. USA* 82:3688, 1985; Hwang et al., *Proc. Natl. Acad. Sci. USA* 77:4030, 1980); EP 52,322; EP 36,676; EP 88,046; EP 143,949; EP 142,641; Japanese Pat. Appl 83-118008; U.S. Pat. Nos. 4,485, 045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal polypeptide therapy.

For parenteral administration, in one embodiment, the polypeptides of the invention are formulated generally by mixing at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; polypeptides, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The therapeutic polypeptide is typically formulated in such vehicles at a concentration of about 0.1 mg/ml to 100 mg/ml, preferably 1-10 mg/ml, at a pH of about 3 to 8. It will be understood that the use of certain of the foregoing excipients, carriers, or stabilizers will result in the formation of polypeptide salts.

Any polypeptide to be used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

Polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous polypeptide solution, and the resulting mixture is lyophilized. The infusion solution is prepared by reconstituting the lyophilized polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

EXAMPLE 15

Method of Treating Decreased Levels of CAN-1, STG and/or SEEK-1 Polypeptide

It will be appreciated that conditions caused by a decrease in the standard or normal expression level of a CAN-1, STG and/or SEEK-1 polypeptide in an individual can be treated by administering a CAN-1, STG and/or SEEK-1 polypeptide of the present invention, as appropriate. Thus, the invention also provides a method of treatment of an individual in need of an increased level of a CAN-1, STG and/or SEEK-1 polypeptide comprising administering to such an individual a pharmaceutical composition comprising an amount of a CAN-1, STG and/or SEEK-1 polypeptide to increase the activity level of the polypeptide in such an individual.

For example, a patient with decreased levels of a CAN-1, STG and/or SEEK-1 polypeptide receives a daily dose 0.1-100 µg/kg of CAN-1, STG and/or SEEK-1 polypeptide for six consecutive days. The exact details of the dosing scheme, based on administration and formulation, are provided in Example 14.

EXAMPLE 16

Method of Treating Increased Levels of CAN-1, STG and/or SEEK-1

Antisense technology is used to inhibit production of a polypeptide of the present invention. This technology is one example of a method of decreasing levels of a polypeptide, preferably a secreted form, due to a variety of etiologies, such as cancer.

For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 14.

Additionally, increased levels of CAN-1 can be treated by using an antibody that specifically binds to CAN-1, thereby reducing the amount of CAN-1 within a cell.

EXAMPLE 17

Method of Treatment Using Gene Therapy

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, et al., *DNA* 7:219, 1988), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

A cDNA encoding a polypeptide of the present invention can be amplified using PCR primers which correspond to the 5' and 3' end sequences respectively as set forth in Example 1. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the polynucleotide of interest properly inserted.

The amphotropic pA317 or GP+am12 packaging cells are grown in tissue culture to confluent density in. Dulbecco's Modified Eagles Medium (DMEM) with 10% calf serum (CS), penicillin and streptomycin. The MSV vector containing the polynucleotide is then added to the media and the packaging cells transduced with the vector. The packaging cells now produce infectious viral particles containing the polynucleotide (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether polypeptide is produced.

The engineered fibroblasts are then transplanted onto the host, either alone or after having been grown to confluence on cytodex 3 microcarrier beads.

EXAMPLE 18

In Situ Hybridization Using CAN-1 as a Probe

This example shows that the expression patterns of CAN-1 mRNA in control and psoriatic skin is consistent with the proposed involvement of the CAN-1 gene product in the development of psoriasis.

Basic architecture of human skin: Human skin is composed of two distinguishable tissue layers. The outermost layer is the epidermis, and is largely (>80%) made of keratinocytes at various stages of differentiation (see below). A basement membrane separates the epidermis from the inner layer of skin, termed the dermis. The dermis is a cellular and fibroelastic connective tissue that is interwoven into a three-dimensional network. The dermis is composed of a complex fabric of interrelated collagen and elastic fibers. See generally Fuchs, Elaine, *Epidermal Differentiation: The Bare Essentials*, The Journal of Cell Biology, Volume 111 (No. 6, Pt. 2), 2807-2814 (December 1990), which is hereby incorporated by reference.

The biology of keratinocyte growth and differentiation in the epidermis: The innermost layer of keratinocytes in the epidermis are called basal cells, and these are predominantly the keratinocytes with the ability to proliferate. There are then four to eight layers of suprabasal spinous cells that are post-mitotic, but metabolically active. Above the spinous layer is then the granular layer where all metabolic activity terminates, and the resulting flattened squames are merely cellular skeletons, filled with macrofibrils of keratin filaments. The outermost layer of the epidermis is the stratum corneum, composed of terminally differentiated keratinocytes sealed together by lipids, which results in the impermeable, insoluble layer necessary to separate the external environment from the body.

In situ hybridization using CAN-1 as a probe: In order to identify the precise component of the human skin that expresses the CAN-1 gene, in situ hybridization was performed using a nucleic acid probe from the CAN-1 gene. These experiments were performed using human skin from a normal healthy control donor, and also from a lesional and an unaffected portion of a psoriatic individual.

The results indicated strong CAN-1 gene expression in the epidermis of a lesion biopsy from a psoriatic patient. In particular, it was noted that hybridization took place predominantly in the upper granular layer, and just beneath the cornified layer. Hybridization was weak to absent in the same relative location in uninvolved biopsy material from a patient, and also from the biopsy of normal healthy skin.

Increased CAN-1 expression in the lesion could have significance in the chemoattraction of inflammatory cell types (neutrophils and monocytes), and also the attraction of T-cells to the sites of psoriatic lesions. In addition, the pattern of CAN-1 expression in a psoriatic lesion could indicate that the aberrant differentiation (e.g., parakanthosis) in the upper epidermis could be related to the increased expression of the CAN-1 protein. It is also possible that the increased CAN-1 expression could play a role in the increased keratinocyte proliferation that is characteristic of psoriatic lesions.

Altered keratinocyte growth and differentiation in psoriasis, and relevance of CAN-1: The underlying pathogenesis of psoriasis involves three predominant and interdependent biologic processes: inflammation (accompanied by T-cell infiltration), epidermal hyperproliferation, and altered differentiation of keratinocytes. The homeostasis of the normal epidermis depends on a balance of growth regulatory signals, which are altered in psoriatic epidermis. Based on the specific location of CAN-1 expression in the epidermis, its small protein size, and its secreted nature, CAN-1 could be useful as an inhibitor of the psoriatic phenotype in any one of these three hallmark biologic processes of psoriatic skin. See generally McKay, MD, Ian A. et al, *Altered Keratinocyte Growth and Differentiation in Psoriasis*, 1995 by Elsevier Science Inc., which is hereby incorporated by reference.

1. Inflammation, and the chemotaxis process: CAN-1 is produced predominantly in the outer granular layer, and the protein could diffuse into the dermis and play a key role in the recruitment of other cell types into the lesional area. These other cell types include a subset of lymphocytes, monocytes, neutrophils, or also endothelial cells. Therefore inhibition of the chemotaxic properties of CAN-1 through the use of a binding partner would be beneficial in the disease state.

2. Keratinocyte proliferation: Over expression of CAN-1 could also act on the basal layer of keratinocytes by providing a signal for proliferation, which is increased in psoriatic lesions. Therefore the inhibition of the proliferation properties of CAN-1 through the use of a binding partner to CAN-1 would be beneficial in the disease state.

3. Keratinocyte differentiation: CAN-1 could act within the granular layer itself to account for the altered pathway of keratinocyte differentiation. In psoriatic skin, there is a pronounced thickening of the cornified layer, as well as an accumulation of nucleated keratinocytes. CAN-1 could control the normal balance between the shedding of the cornified layer, and the keratinocyte proliferation in the basal layer. The use of a binding partner to CAN-1 could reduce the effects of excess CAN-1 in the skin.

EXAMPLE 19

Hybridization Protocol

This example describes a representative hybridization protocol that can be used to identify nucleic acid molecules of the invention (such as cDNA and genomic DNA molecules) that hybridize to a nucleic acid probe under defined conditions.

Hybridization solution should preferably be prepared and filtered through a 0.45-micron disposable cellulose acetate filter. The composition of the hybridization solution is 6×SSC, 5×Denhardt's reagent, 0.5% sodium dodecyl sulfate (SDS), 100 µg/ml denatured, fragmented salmon sperm DNA.

Denhardt's reagent is utilized in nucleic acid hybridization solutions. 500 ml of 50×Denhardt's reagent (the 50-fold concentrate) includes 5 g Ficoll (Type 400, Pharmacia), 5 g polyvinylpyrrolidone, 5 g bovine serum albumin (Fraction V, Sigma) and water to a final volume of 500 ml.

The nitrocellulose filter or nylon membrane containing the target DNA (e.g., a putative CAN-1 cDNA) is floated on the surface of a tray of 6×SSC until it becomes thoroughly wetted from beneath. The filter is submerged for 2 minutes and then slipped into a heat-sealable bag. 0.2 ml of hybridization solution is added for each square centimeter of nitrocellulose filter or nylon membrane.

As much air as possible is squeezed from the bag, and the open end of the bag is sealed with a heat sealer. The bag is incubated for 1-2 hours submerged at the desired temperature (typically no higher than the hybridization temperature). It is desirable to agitate the bag.

If the radiolabeled probe is double-stranded, it is denatured by heating for 5 minutes at 100° C. Single-stranded probe need not be denatured. The denatured probe is chilled rapidly in ice water. Ideally, probe having a specific activity of $10^9$ cpm/µg, or greater, is used. Hybridization is carried out for the desired time period at 50° C., typically using 1-2 µg/ml radiolabeled probe. The probe can be, for example, a nucleic acid molecule consisting of the complement of the nucleic acid sequence set forth in SEQ ID NO:1.

The bag containing the filter is quickly removed from the water bath and opened by cutting off one corner with scissors. The denatured probe is added to the hybridization solution, and then as much air as possible is squeezed from the bag which is then resealed with the heat sealer so that as few bubbles as possible are trapped in the bag. To avoid radioactive contamination of the water bath, the resealed bag should be sealed inside a second, noncontaminated bag.

The bag is submerged in a water bath for the required period of hybridization (for example, 16 hours) at 50° C. The bag is removed from the water bath and one corner is cut off. The hybridization solution is poured into a container suitable for disposal, and then the bag is cut along the length of three sides. The filter is removed and immediately submerged in a tray containing several hundred milliliters of 2×SSC and 0.5% SDS at room temperature (no higher than 25° C.). The filter should not be allowed to dry out at any stage during the washing procedure.

After 5 minutes, the filter is transferred to a fresh tray containing several hundred milliliters of 2×SSC and 0.1% SDS, and incubated for 15 minutes at room temperature (no higher than 25° C.) with occasional gentle agitation. The filter should then be washed at the desired stringency, i.e., in the desired concentration of SSC and at the desired temperature. If, for example, nucleic acid molecules that hybridize to the probe at a temperature of 55° C. in 2×SSC are sought, then the filter is washed in 2×SSC at 55° C., i.e., nucleic acid molecules that do not hybridize to the probe under conditions of 2×SSC at 55° C. are washed off. Washing can be done for any desired time period, such as one hour, with several changes of washing solution.

Most of the liquid is then removed from the filter by placing the filter on a pad of paper towels. The damp filter is then placed on a sheet of Saran Wrap. Adhesive dot labels marked with radioactive ink are applied to several asymmetric locations on the Saran Wrap. These markers serve to align the autoradiograph with the filter. The labels are covered with Scotch Tape which prevents contamination of the film holder or intensifying screen with the radioactive ink. Radioactive ink is made by mixing a small amount of $^{32}P$ with waterproof black drawing ink. A fiber-tip pen can be used to apply ink to the adhesive labels.

The filter is covered with a second sheet of Saran Wrap, and exposed to X-ray film (Kodak XAR-2 or equivalent) to obtain an autoradiographic image. The exposure time should be determined empirically.

From the foregoing, it may be seen that this invention is one well-adapted to achieve all the ends and objects hereinabove set forth together with other advantages which are obvious and which are inherent to the invention. It will be understood that certain features and subcombinations are of utility and may be employed without reference to other features and subcombinations. The above examples discuss the techniques and procedures utilized and are considered to be the preferred embodiment of the current invention, and it is understood that there are many other techniques and procedures that could be employed which would allow an individual of ordinary skill in the art to perform the claimed invention. Such other techniques and procedures are contemplated by and are within the scope of the claims. Since many possible embodiments may be made of the invention without departing from the scope thereof, it is to be understood that all matter herein set forth and shown in the examples are to be interpreted as illustrative and not in a limiting sense.

The embodiments of the invention in which an exclusive property or privilege is claimed are defined as follows:

1. An isolated cDNA molecule comprising of the nucleic acid sequence set forth in SEQ ID NO:10.

2. A method of making an isolated CAN-1 polypeptide comprising:
   (a) culturing a host cell comprising a vector comprising a nucleic acid molecule of claim 1 under conditions that enable expression of the encoded CAN-1 polypeptide; and
   (b) recovering said expressed polypeptide.

3. An isolated vector comprising a nucleic acid molecule of claim 1.

4. An isolated host cell comprising a vector of claim 3.

5. A method of making an isolated CAN-1, polypeptide comprising: (a) culturing a host cell comprising a vector of claim 3 comprising a nucleic acid molecule of SEQ ID NO:10 encoding a CAN-1 polypeptide under conditions that enable expression of said CAN-1 polypeptide; and (b) recovering said expressed polypeptide.

* * * * *